(12) United States Patent
Smith et al.

(10) Patent No.: US 12,083,228 B2
(45) Date of Patent: Sep. 10, 2024

(54) METHODS AND COMPOSITIONS FOR TREATING RESPIRATORY DISEASE

(71) Applicant: NOVAVAX, INC., Gaithersburg, MD (US)

(72) Inventors: Gale Smith, Germantown, MD (US); Ye Liu, Clarksville, MD (US); Jing-Hui Tian, Germantown, MD (US); Michael J. Massare, Mt. Airy, MD (US); Sarathi Boddapati, Germantown, MD (US); Gregory Glenn, Poolesville, MD (US); Louis Fries, Ellicott City, MD (US); Iksung Cho, Potomac, MD (US)

( * ) Notice: Subject to any disclaimer, the term of this patent is extended or adjusted under 35 U.S.C. 154(b) by 1050 days.

(21) Appl. No.: 16/629,859

(22) PCT Filed: Jul. 24, 2018

(86) PCT No.: PCT/US2018/043431
§ 371 (c)(1),
(2) Date: Mar. 29, 2021

(87) PCT Pub. No.: WO2019/023196
PCT Pub. Date: Jan. 31, 2019

(65) Prior Publication Data
US 2021/0137845 A1    May 13, 2021

Related U.S. Application Data

(60) Provisional application No. 62/536,235, filed on Jul. 24, 2017.

(51) Int. Cl.
| A61K 9/51 | (2006.01) |
| A61K 39/155 | (2006.01) |
| A61P 11/00 | (2006.01) |
| A61P 31/14 | (2006.01) |

(52) U.S. Cl.
CPC .......... *A61K 9/5123* (2013.01); *A61K 39/155* (2013.01); *A61P 11/00* (2018.01); *A61P 31/14* (2018.01); *C12N 2760/16022* (2013.01); *C12N 2760/16034* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| 4,900,549 A | 2/1990 | De Vries et al. |
| 5,057,540 A | 10/1991 | Kensil et al. |
| 5,149,650 A | 9/1992 | Wertz et al. |
| 5,620,690 A | 4/1997 | Kersten et al. |
| 6,231,859 B1 | 5/2001 | Kensil |
| 6,245,532 B1 | 6/2001 | Smith et al. |
| 6,352,697 B1 | 3/2002 | Cox et al. |
| 6,428,807 B1 | 8/2002 | MacFarlan et al. |
| 6,558,670 B1 | 5/2003 | Friede et al. |
| 8,563,002 B2 | 10/2013 | Baudoux et al. |
| 8,715,692 B2 | 5/2014 | Pushko et al. |
| 8,821,881 B2 | 9/2014 | Morein et al. |
| 9,675,685 B2 | 6/2017 | Pushko et al. |
| 9,708,373 B2 | 7/2017 | Garcia-Sastre et al. |
| 9,717,786 B2 | 8/2017 | Pushko et al. |
| 9,731,000 B2 | 8/2017 | Pushko et al. |
| 10,022,437 B2 | 7/2018 | Pushko et al. |
| 10,426,829 B2 * | 10/2019 | Smith ..................... A61P 31/16 |
| 10,729,764 B2 | 8/2020 | Morein et al. |
| 11,052,146 B2 | 7/2021 | Pushko et al. |
| 11,253,585 B2 * | 2/2022 | Smith ..................... A61P 31/16 |
| 2004/0028698 A1 | 2/2004 | Colau et al. |
| 2005/0142148 A1 | 6/2005 | Fouchier et al. |
| 2006/0121065 A1 | 6/2006 | Morein et al. |
| 2006/0171917 A1 | 8/2006 | Campbell et al. |
| 2006/0239963 A1 | 10/2006 | Morein et al. |
| 2008/0233150 A1 | 9/2008 | Smith et al. |
| 2009/0257980 A1 | 10/2009 | Davies et al. |
| 2010/0239617 A1 | 9/2010 | Pushko et al. |
| 2010/0239671 A1 | 9/2010 | Edelman et al. |
| 2010/0285135 A1 | 11/2010 | Wendorf et al. |
| 2010/0291147 A1 | 11/2010 | Baudoux et al. |
| 2012/0107353 A1 | 5/2012 | Morein et al. |
| 2013/0011443 A1 | 1/2013 | Fattom et al. |
| 2013/0064867 A1 | 3/2013 | Fattom et al. |

(Continued)

FOREIGN PATENT DOCUMENTS

| AU | 2003245220 B2 | 4/2009 |
| AU | 2014100888 A4 | 9/2014 |
| CA | 2491457 C | 9/2012 |
| CN | 101090711 A | 12/2007 |
| CN | 102107003 A | 6/2011 |
| EP | 0109942 A2 | 5/1984 |
| EP | 0362279 B1 | 1/1995 |
| EP | 1539231 B1 | 6/2009 |
| JP | 2012533558 A | 12/2012 |

(Continued)

OTHER PUBLICATIONS

Cimen et al. (Respiratory Care. Feb. 2015; 60 (2): 239-243).*

(Continued)

*Primary Examiner* — Shanon A. Foley

(74) *Attorney, Agent, or Firm* — Carlson, Caspers, Vandenburgh & Lindquist, P.A.

(57) ABSTRACT

Disclosed herein are methods and nanoparticles suitable for use in reducing exacerbations in COPD patients. The methods and compositions advantageously reduce the incidence of hospitalization in COPD patients that occurs in response to environmental insults such as exposure to or infection by RSV. Dosages, formulations, and methods for preparing the vaccines and nanoparticles are also disclosed.

18 Claims, 4 Drawing Sheets

Specification includes a Sequence Listing.

(56) References Cited

U.S. PATENT DOCUMENTS

| | | |
|---|---|---|
| 2013/0122032 A1 | 5/2013 | Smith et al. |
| 2013/0123333 A1 | 5/2013 | Mirkin et al. |
| 2013/0337005 A1 | 12/2013 | Rademacher et al. |
| 2014/0227309 A1 | 8/2014 | Smith et al. |
| 2014/0294879 A1 | 10/2014 | Pushko et al. |
| 2014/0335049 A1 | 11/2014 | Morein et al. |
| 2015/0202283 A1 | 7/2015 | Steff et al. |
| 2015/0209425 A1 | 7/2015 | Morein et al. |
| 2015/0265698 A1 | 9/2015 | Pushko et al. |
| 2015/0266930 A1 | 9/2015 | Pushko et al. |
| 2015/0306207 A1 | 10/2015 | Smith et al. |
| 2015/0320854 A1 | 11/2015 | Radosevic et al. |
| 2015/0335730 A1 | 11/2015 | Smith et al. |
| 2015/0359872 A1 | 12/2015 | Pushko et al. |
| 2016/0184427 A1 | 6/2016 | Morein et al. |
| 2017/0202948 A1 | 7/2017 | Smith et al. |
| 2017/0319682 A1 | 11/2017 | Smith et al. |
| 2018/0133308 A1 | 5/2018 | Smith et al. |
| 2018/0346521 A1 | 12/2018 | Langedijk |
| 2018/0369368 A1 | 12/2018 | Morein et al. |
| 2019/0134187 A1 | 5/2019 | Pushko et al. |
| 2019/0314487 A1 | 10/2019 | Boddapati et al. |
| 2020/0030436 A1 | 1/2020 | Pushko et al. |
| 2020/0101151 A1 | 4/2020 | Smith et al. |
| 2020/0215189 A1 | 7/2020 | Morein et al. |
| 2021/0137845 A1* | 5/2021 | Smith ............... A61P 31/14 |

FOREIGN PATENT DOCUMENTS

| | | |
|---|---|---|
| JP | 2014500013 A | 1/2014 |
| JP | 2014520807 A | 8/2014 |
| JP | 2014526471 A | 10/2014 |
| JP | 2014530010 A | 11/2014 |
| JP | 2015171378 A | 10/2015 |
| WO | WO-8809336 A1 | 12/1988 |
| WO | WO-9003184 A1 | 4/1990 |
| WO | WO-9100104 A1 | 1/1991 |
| WO | WO-9611711 A1 | 4/1996 |
| WO | WO-9730728 A1 | 8/1997 |
| WO | WO-20010066137 A1 | 9/2001 |
| WO | WO-2004004762 A1 | 1/2004 |
| WO | WO-2005002620 A1 | 1/2005 |
| WO | WO-2005021713 A2 | 3/2005 |
| WO | WO-2005080417 A2 | 9/2005 |
| WO | WO-2007149490 A1 | 12/2007 |
| WO | WO-2008114149 A2 | 9/2008 |
| WO | WO-2008133663 A2 | 11/2008 |
| WO | WO-2009012487 A2 | 1/2009 |
| WO | WO-2009108689 A1 | 9/2009 |
| WO | WO-2010077717 A1 | 7/2010 |
| WO | WO-2010138193 A2 | 12/2010 |
| WO | WO-2012061815 A2 | 5/2012 |
| WO | WO-2013006842 A2 | 1/2013 |
| WO | WO-2013049342 A1 | 4/2013 |
| WO | WO-2014024024 A1 | 2/2014 |
| WO | WO-2014124423 A1 | 8/2014 |
| WO | WO-2014174018 A1 | 10/2014 |
| WO | WO-2015042373 A1 | 3/2015 |
| WO | WO 2017/041100 * | 3/2017 |
| WO | WO-2017041100 A2 | 3/2017 |
| WO | WO 2017/102737 A1 | 6/2017 |

OTHER PUBLICATIONS

Talbot et al. (Clinical Practice. Nov. 2016; 24 (6): 295-302).*
Kokyu to Junkan [Respiration and circulation] (2012) vol. 60, No. 1, p. 69-77, 15 pages, including partial English translation.
De Serres, G.D., "Importance of viral and bacterial infections in chronic obstructive pulmonary disease exacerbations", Journal of Clinical Virology, (2009) vol. 46, issue 2, p. 129-133.
Smith, L.H.Jr. and Wyngaarden, J.B. et al., editors, chief translator Wu Xiubin, et al., Goldman's Cecil Medicine, Cecil Textbook of Medicine, 3(19):586-589 (1995).
Wang Chen et al., "New Advances in Respiratory Diseases," People's Military Medical Press, p. 51(2011).
Zwaans, W.A.R., et al., "The relevance of respiratory viral infections in the exacerbations of chronic obstructive pulmonary disease—A systematic review", Journal of Clinical Virology, (2014) vol. 61, issue 2, p. 181-188.
International Search Report and Written Opinion issued by the International Searching Authority for Application No. PCT/US2018/0434131, dated Oct. 31, 2018, 9 pages.
Broadbent et al. "Chapter 59: Respiratory Virus Vaccines," Mucosal Immunology, 4th Edition 1:1129-1170 (2015).
Adjuvanting Viral Vectored Malaria Vaccines with Matrix M, Identifier NCT01669512, ClinicaiTrials.gov, U.S. National Institutes of Health; available at http://clinicaltrials.gov/ct2/show/NCT01669512?term=MatrixM+or+Matrix+M&rank=1, Mar. 9, 2014, pp. 1-4.
"Safety Evaluation of Certain Food Additives and Contaminants Quillaia Extracts," WHO Food Additives, WHO (first draft, Eastwood et al., Series:48, pp. 1-14 (2001).
Ahlberg et al., Global transcriptional response to ISCOM-Matrix adjuvant at the site of administration and in the draining lymph node early after intramuscular injection in pigs, Developmental and Comparative Immunology, vol. 38, pp. 17-26 (2012), Elsevier Ltd.
Anderson et al., "Intracellular processing of the human respiratory syncytial virus fusion glycoprotein: amino acid substitutions affecting folding, transport and cleavage," J. Gen. Virol. 73:1177-118 (1992).
Anonymous, "Novavax Announces Topline RSV F Vaccine Data from Two Clinical Trials in Older Adults," dated Sep. 15, 2016, 3 pages.
Barr et al., "ISCOMs and other saponin based adjuvants," Advanced Drug Delivery Reviews, (1998), 32: 247-271.
Behboudi et al., "Quillaja Saponin Formulations that Stimulate Proinflammatory Cytokines Elicit a Potent Acquired Cell-Mediated Immunity," Scand. J. Immunol. 50:371-377 (1999).
Bengtsson et al., Matrix-M adjuvant increases immunogenicity of seasonal influenza vaccine for the elderly, manuscript in preparation, pp. 1-27 (2014).
Boulter, et al., Evaluation of recombinant sporozoite antigen SPAG-1 as a vaccine candidate against Theileria annulata by the use of different delivery systems, Tropical Medicine and International Health, vol. 4, pp. A71-A77 (1999), Blackwell Science, Ltd.
Brandenburg et al., Respiratory Syncytial Virus Specific Serum Antibodies in Infants Under Six Months of Age: Limited Serological Response Upon Infection, J. Med. Virol. 52:97-104 (1997).
Calder et al., "Electron Microscopy of the Human Respiratory Syncytial Virus Fusion Protein and Complexes That It Forms with Monoclonal Antibodies," Virol. 271:122-131 (2000).
Citovsky et al., "Fusion of Sendai Virions or Reconstituted Sendai Virus Envelopes with Liposomes or Erythrocyte Membranes Lacking Virus Receptors," The Journal of Biological Chemistry 260(22)12072-12077 (1985).
"Committee for Veterinary Medicinal Products, Quillaia Saponins, Summary Report", The European Agency for the rgJ Evaluation of Medicinal Products, EMEA/MRL/055/95-FINAL, Feb. 1996, pp. 1-2.
Copland et al., "Hydration of lipid films with an aqueous solution of Quil A: a simple method for the preparation of immune-stimulating complexes," International Journal of Pharmaceutics 196:135-139 (2000).
Coulter, et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.
Cox, et al., Development of an Influenza-ISCOM Vaccine, in Vaccine Design (eds. G. Gregoriadis et al.), Springer Science+Business Media, New York (1997), pp. 33-49.
Cox, et al., Evaluation of a virosomal H5N1 vaccine formulated with Maxtrix M adjuvant in phase I clinical trial, Elsevier Ltd, Vaccine, 29, pp. 8049-8059, Aug. 22, 2011.
Cox, et al., Prospects for the Development of New Vaccine Adjuvants, BioDrugs, vol. 12(6), pp. 439-453 (1999), Ad is International Limited.

(56) References Cited

OTHER PUBLICATIONS

Creemers et al., "Endoproteolytic Cleavage of Its Propeptide Is a Prerequisite for Efficient Transport of Furin Out of the Endoplasmic Reticulum," J. Biol. Chem. 270(6):2695-2702 (1995).
Crowe, Jr. et al. "Passively Acquired Antibodies Suppress Humoral But Not Cell-Mediated Immunity in Mice Immunized with Live Attenuated Respiratory Syncytial Virus Vaccines," J. Immunol. 167:3910-3918 (2001).
Crowe, Jr. "Influence of Maternal Antibodies on Neonatal Immunization against Respiratory Viruses," Clin. Infect. Dis. 33:1720-1727 (2001).
Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).
Demana et al., "Pseudo-ternary phase diagrams of aqueous mixtures of Quil A, cholesterol and phospholipid prepared by the lipid-film hydration method," International Journal of Pharmaceutics 270:229-239 (2004).
Demirjian and Levy, "Safety and Efficacy of Neonatal Vaccination," Eur. J. Immunol. 39(1):36-46 (2009).
Drane et al., "Iscomatrix adjuvant for prophylactic and therapeutic vaccines," Expert Rev. Vaccines 6:761-772 (2007).
Eckert et al., "Mechanisms of Viral Membrane Fusion and Its Inhibitionm," Annual Review of Biochemistry 70:770-810 (2001).
Ekstrom et al., "Iscom and iscom-matrix enhance by intranasal route the IgA responses to OVA and rCTB in local and remote mucosal secretions," Vaccine 17:2690-2701 (1999).
Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).
Extended European Search Report issued by the European Patent Office for Application No. 18838914.2, dated Mar. 2, 2021, 9 pages.
Eyles et al., "Immunodominant Francisella tularensis antigens identified using proteome microarray," Proteomics 7:2172-2183 (2007).
Fossum et al., Early inflammatory response to the saponin adjuvant Matrix-M in the pig, Veterinary Immunology and Immunopathology, http://dx.doi.org/10.1 016/j.vetimm.2013.07.007 (2013), pp. 1-9, Elsevier B.V.
Genbank Accession No. AAC55970.1, "fusion glycoprotein precursor [Human respiratory syncytial virus]" (1996), 1 page.
Genocea Biosciences, Genocea Reports Positive Initial Phase 1/2A Results for GEN-003, It's Pioneering Therapeutic Vaccine Candidate for the Treatment of Herpes Simplex Virus-2 (HSV-2), at ICAAC 2013, press release, Cambridge MA, Sep. 12, 2013, pp. 1-3.
Giannos et al., Formulation Stabilization and Disaggregatoin of Bevacizumab, Ranibizumab and Aflibercept in Dilute Solutions, Pharm Res 35:78 (2018), 15 pages.
Glenn et al., "A Randomized, Blinded, Controlled, Dose-Ranging Study of a Respiratory Syncytial Virus Recombinant Fusion (F) Nanoparticle Vaccine in Healthy Women of Childbearing Age," The Journal of Infectious Diseases 213:411-422 (2016).
Glenn et al., "Safety and immunogenicity of a Sf9 insect cell-derived respiratory syncytial virus fusion protein nanoparticle vaccine," Vaccine. Jan. 7, 2013;31(3):524-532.
Glenn, "Recombinant, Insect Cell-Derived RSV Nanoparticle Vaccine," Novavax.com, 34 pages (Jul. 4, 2012) https://www.novavax.com/download/file/RSV nanoparticle Vaccine-MVADsJuly4(2).pdf.
Gonzalez-Reyes et al., "Cleavage of the human respiratory syncytial virus fusion protein at two distinct sites is required for activation of membrane fusion," Proc. Natl. Acad. Sci. USA 98(17):9859-9864 (2001).
Gruenke et al., "New Insights into the Spring-Loaded Conformational Change of Influenza Virus Hemagglutinin," Journal of Virology, May 2002, 76:(9) 4456-4466 (2002).
Halsey and Galazka, "The efficacy of DPT and oral poliomyelitis immunization schedules initiated from birth to 12 weeks of age," Bull. World Health Org. 63(6):1151-1169 (1985).
Hancock et al., "Adjuvants Recognized by Toll-Like Receptors Inhibit the Induction of Polarized Type 2 T Cell Responses by Natural Attachment (G) Protein of Respiratory Syncytial Virus," Vaccine 21(27-30):4348-4358 (2003).
Higgins et al., "Advances in RSV vaccine research and development—A global agenda," Vaccine 34:2870-2875 (2016).
Iyer et al., Purified, Proteolytically Mature HIV Type 1 SOSIP gp140 Envelope Trimers, AIDS Research and Human Retroviruses 23(6):817-828 (2007).
Johansson et al., "Iscoms with different quillaja saponin components differ in their immunomodulating activities," Vaccine 17:2894-2900 (1999).
Kanekiyo et al., "Self-assembling influenza nanoparticle vaccines elicit broadly neutralizing H1N1 antibodies," Nature 2013, vol. 499 p. 102-108.
Karin Lovgren Bengtsson, Bror Morein & Albert DME Osterhaus (2011) ISCOM technology-based Matrix M adjuvant: success in future vaccines relies on formulation, Expert Review of Vaccines, 10:4, 401-403, DOI: 10.1586/erv.11.25.
Kensil, Saponins as Vaccine Adjuvants, Critical Reviews in Therapeutic Drug Carrier Systems, vol. 13(1&2), pp. 1-55 (1996), Begell House, Inc.
Kersten et al., On the structure of immune-stimulating saponin-lipid complexes (iscoms) Biochimica et Biophysica Acta, 1062:165-171 (1991).
Kim et al., "Respiratory Syncytial Virus Disease in Infants Despite Prioir Administration of Antigenic Inactivated Vaccine," Am. J. Epidemil. 89(4):422-434 (1969).
Lavelle et al., "Cholera Toxin Promotes the Induction of Regulatory T Cells Specific for Bystander Antigens by Modulating Dendritic Cell Activation," Journal of Immunology 171:2384-2392 (2003).
Lee et al., "Recent Advances of Vaccine Adjuvants for Infectious Diseases," Immune Network, 51-57 (2015).
Lichtenberg et al., "The Mechanism of Detergent Solubilization of Lipid Bilayers," Biophysical Journal, vol. 105:289-299 (2013).
Lieberman et al., "Preparation and immunogenic properties of a recombinant West Nile subunit vaccine," Vaccine 25:414-423 (2007).
Lovgren et al., The Requirement of Lipids for the Formation of Immunostimulating Complexes (Iscoms), Biotechnol. Appl. Biochem. 10:161-172 (1988).
Lovgren-Bengtsson, 6 Preparation and Use of Adjuvants; Methods in Microbiology, vol. 25, pp. 471-502 (1998), Academic Press Ltd.
Lovgren-Bengtsson et al., "4.5 Preparation and Use of Adjuvants," Methods in Microbiology 32:551-588 (2002).
Lucy et al., "Structure and Assembly of Macromolecular Lipid Complexes Composed of Globular Micelles," Journal of Molecular Biology, (1964), 8: 727-748.
Magnusson et al., Immune enhancing properties of the novel Matrix-M adjuvant leads to potentiated immune responses to an influenza vaccine in mice, Vaccine, http://dx.doi.org/10.1016/j.vaccine.2013.01.039 (2013), pp. 1-9, Elsevier Ltd.
Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.
Makwana et al., "Prefilled Syringes: An Innovation in Parenteral Packaging," International Journal of Pharmaceutical Investigation 1(4):200-206 (2011).
Martin et al., "Sequence elements of the fusion peptide of human respiratory syncytial virus fusion protein required for activity," J. Gen. Virol. 87:1649-1658 (2006).
Martinez et al., "Combining DNA and protein vaccines for early life immunization against respiratory syncytial virus in mice," Eur. J. Immunol. 29:3390-3400 (1999).
McKenzie et al., ISCOMATRIX vaccines: Safety in human clinical studies, Human Vaccines, vol. 6, No. 3, pp. 237-246 (2010), Landes BioScience.
Morein et al., "Current status and potential application of ISCOMs in veterinary medicine," Advanced Drug Delivery Reviews 56:1367-1382 (2004).
Murphy et al., "An update on approaches to the development of respiratory syncytial virus (RSV) and parainfluenza virus type 3 (PIV3) vaccines," Virus Res. 32:13-26 (1994).

(56) References Cited

OTHER PUBLICATIONS

Murphy et al., "Effect of Age and Preexisting Antibody on Serum Antibody Response of Infants and Children to the F and G Glycoproteins during Respiratory Syncytial Virus Infection," J. Clin. Microbiol. 24(5):894-898 (1986).

Murphy et al., "Effect of passive antibody on the immune repsone of cotton rats to purified F and G glycoproteins of repiratory suncytial virus (RSV)," Vaccine 9:185-189 (1991).

Murphy et al., "Passive Transfer of Respiratory Syncytial Virus (RSV) Antiserum Suppresses the Immune Response to the RSV Fusion (F) and Large (G) Glycoproteins Expressed by Recombinant Vacccinia Viruses," J. Virol. 62(10):3907-3910 (1988).

"Novavax NanoFlu Achieves All Primary Endpoints In Phase 3 Clinical Trial," Press Release dated Mar. 24, 2020, 3 pages.

Nussbaum et al., "Fusion of influenza 'Virus particles with liposomes: requirement for cholesterol and virus receptors to allow fusion with and lysis of neutral but not of negatively charged liposomes",. Journal of General Virology, 2831-2837 (1992).

Ozel et al., "Quaternary Structure of the Immunostimulating Complex (Iscom)," Journal of Ultrastructure and Molecular Structure Research 102:240-248 (1989).

Parrington et al., "Baculovirus expression of the respiratory syncytial virus fusion protein using Trichoplusia ni insect cells," Virus Genes 14:63-72 (1997).

Pedersen et al., Matrix-M adjuvanted virosomal H5N1 vaccine confers protection against lethal viral challenge in a murine model, Influenza and Other Respiratory Viruses. DOI: 10.1111/j.1750-2659.2011.00256.x (2011 ), pp. 1-12, Blackwell Publishing Ltd.

Pedersen, et al.; T-Helper 1 Cells Elicited by H5N1 Vaccination Predict Seroprotection, Journal of Infectious Disease, 206, pp. 158-166, Jul. 15, 2016.

Rama et al., "An insect cell derived respiratory syncytial virus (RSV) F nanoparticle vaccine induces antigenic site II antibodies and protects against RSV challenge in cotton rats by active and passive immunization", Vaccine, Elsevier, Amsterdam, NL, 32(48)6485-6492 (2014).

Rimmelzwaan et al., A randomized, double blind study in young healthy adults comparing cell mediated and 1 humoral immune responses induced by influenza ISCOM vaccines and conventional vaccines; Vaccine, 2001, vol. 19, pp. 1180-1187, Elsevier Science Limited.

Roder, et al., "Purification of respiratory syncytial virus F and G-proteins," Journal of Chromatography B: Biomedical Sciences and Applications 737:97-106 (2000).

Ronnberg et al., "Adjuvant activity of non-toxic Quillaja saponaria Molina components for use in ISCOM matrix," Vaccine, vol. 13, No. 14, pp. 1375-1382 (1995).

Ruiz-Arguello et al., "Effect of Proterlytic Processing at Two Distinct Sites on Shape and Aggregation of an Anchorless Fusion Protein of Human Respiratory Syncytial Virus and Fate of the Intervening Segment," Virol. 298:317-326 (2002).

Ruiz-Arguello et al., "Thermostability of the human respiratory syncytial virus fusion protein before and after activation: implications for the membrane-fusion mechanism," J. Gen. Virol. 85:3677-3687 (2004).

Safety and Immunogenicity Study of Therapeutic HSV-2 Vaccine, Identifier NCT01667341, ClinicaiTrials.gov, U.S. National Institutes of Health; available at http://clinicaltrials.gov/ct2/show/NCT01667341 ?term=matrix+m&rank=3, Mar. 9, 2014, pp. 1-4.

Sales and Wang, "Respiratory syncytial virus vaccine: Is it coming?" Paediatr. Child Health 8(10):605-608 (2003).

Shi et al., "Stabilization of Human Papillomavirus Virus-Like Particles by Non-Ionic Surfactants," Journal of Pharmaceutical Sciences, 2005, p. 1538-1551.

Shinde et al., "Improved Titers Against Influenza Drift Variants with a Nanoparticle Vaccine," N Engl Med 378:24 (2018), 3 pages.

Shinde et al., "Induction of Broadly Cross-Reactive Immune Responses Against A(H3N2) Viruses: Results of a Phase 2 Trial of a Novel Recombinant Hemagglutinin Saponin-Adjjvanted nanoparticle Influenza Vaccine (NanoFlu")", 30 pages (2018).

Siegrist et al., "Protective Efficacy against Respiratory Syncytial Virus following Murine Neonatal Immunization with BBG2Na Vaccine: Influence of Adjuvants and Maternal Antibodies," J. Infect. Dis. 179:1326-1333 (1999).

Siegrist, "Mechanisms by which maternal antibodies influence infant vaccine responses: review of hypotheses and definition of main determinants," Vaccine 21:3406-3412 (2003).

Sjolander, et al., ISCOMs: an adjuvant with multiple functions, Journal of Leukocyte Biology, vol. 64, pp. 713-723 (1998).

Sjolander, et al., Uptake and adjuvant activity of orally delivered saponin and ISCOM vaccines, Advanced Drug Delivery Reviews, vol. 34, pp. 321-338 (1998), Elsevier Science B.V.

Skoberne et al., An adjuvanted herpes simplex virus 2 subunit vaccine elicits a T cell response in mice and is an effective therapeutic vaccine in Guinea pigs, J. Virol. 87:3930-3942 (2013).

Smith et al., "Novel hemagglutinin nanoparticle influenza vaccine with Matrix-M adjuvant induces hemagglutination inhibition, neutralizing, and protective responses in ferrets against homologous and drifted A(H3N2) subtypes," Vaccine 35:5366-5372 (2017).

Smith et al., "Respiratory Syncytial Virus Fusion Glycoprotein Expressed in Insect Cells Form Protein Nanoparticles That Induce Protective Immunity in Cotton Rats," PLOS One 7(11):e50852, 12 pages (2012).

Sun et al., "Advances in saponin-based adjuvants," Vaccine 27:1787-1796 (2009).

Sun et al., "ISCOMs and ISOMATRIX," Vaccine 27:4388-4401 (2009).

Tekewe et al., A rapid and simple screening method to identify conditions for enhanced stability of modular vaccine candidates, Biochemical Engineering Journal 100:50-58 (2015).

Vaarala et al., "Antigenic Differences between AS03 Adjuvanted Influenza A (H1N1) Pandemic Vaccines: Implications for Pandemrix Associated Narcolepsy Risk," PLOS One, 1-23 (2014).

Wald, "A Novel Therapeutic Vaccine (GEN003) for Genital Herpes Reduces HSV-2 Shedding: Initial Results of Clinical Trial GEN003-001," Presented at Interscience Conference on Antimicrobial Agents and Chemotherapy (ICAAC 2013), Denver, CO, Sep. 12, 2013, pp. 1-21.

Wald et al., Novel Therapeutic Vaccine for Genital Herpes Reduces Genital HSV-2 Shedding, in ICAAC 2013, Denver, CO, Sep. 2013, cover page and p. 279, Abstract 183(G).

Wang et al., "Expression and purification of an influenza hemagglutinin-one step closer to a recombinant protein-based influenza vaccine," Vaccine vol. 24, Issue 12, pp. 2176-2185 (2006).

Wang, "Protein aggregation and its inhibition in biopharmaceutics," International Journal of Pharmaceutics 289 (2005) 1-30.

Wathen et al., Immunization of Cotton Rats with the Human Respiratory Syncytial Virus F Glycoprotein produced using a Baculovirus Vector, The Journal of Infectious Diseases 159(2):255-264 (1989).

Weisshaar et al., "Blocking Respiratory Syncytial Virus Entry: A Story with Twists," DNA Cell Biol. 34:505-510 (2015).

Whitehead et al., "Recombinant Respiratory Syncytial Virus (RSV) Bearing a Set of Mutations from Cold-Passaged RSV is Attenuated in Chimpanzees," J. Virol. 72(5):4467-4471 (1998).

Widjaja et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One 10(6):e0130829, 19 pages (2015).

Wu et al., "Active 1918 pandemic flu viral neuraminidase has distinct N-glycan profile and is resistant to trypsin digestion," Biochemical and Biophysical Research, 2009, vol. 379. p. 749-753.

\* cited by examiner

Fig. 1. RSV F Protein Functional Sites 1 pQNITEEFYQS TCSAVSKGYL SALRTGWYTS VITIELSNIK ENKCNGTDAK

51 VKLIKQELDK YKNAVTELQL LMQSTPATNN RARRELPRFM *NYTLNNAKKT*

*101 NVTLSKKQKQ QAIASGVAVS KVLHLEGEVN KIKSALLSTN KAVVSLSNGV*

*151 SVLTSKVLDL KNYIDKQLLP IVNKQSCSIS NIETVIEFQQ KNNRLLEITR*

*201 EFSVNAGVTT PVSTYMLTNS ELLSLINDMP ITNDQKKLMS NNVQIVRQQS*

*251 YSIMSIIKEE VLAYVVQLPL YGVIDTPCWK LHTSPLCTTN TKEGSNICLT*

*301 RTDRGWYCDN AGSVSFFPQA ETCKVQSNRV FCDTMNSLTL PSEVNLCNVD*

*351 IFNPKYDCKI MTSKTDVSSS VITSLGAIVS CYGKTKCTAS NKNRGIIKTF*

*401 SNGCDYVSNK GVDTVSVGNT LYYVNKQEGK SLYVKGEPII NFYDPLVFPS*

*451 DEFDASISQV NEKINQSLAF IRKSDELLHN VNAGKSTTNI MITTIIIVII*

*501 VILLSLIAVG LLLYCKARST PVTLSKDQLS GINNIAFSN*

Legend:

F1 domain in *italics*, F2 domain underlined, N-Linked glycosylation site, -Furin cleavage site, - major cleavage site

- Disulfide bond

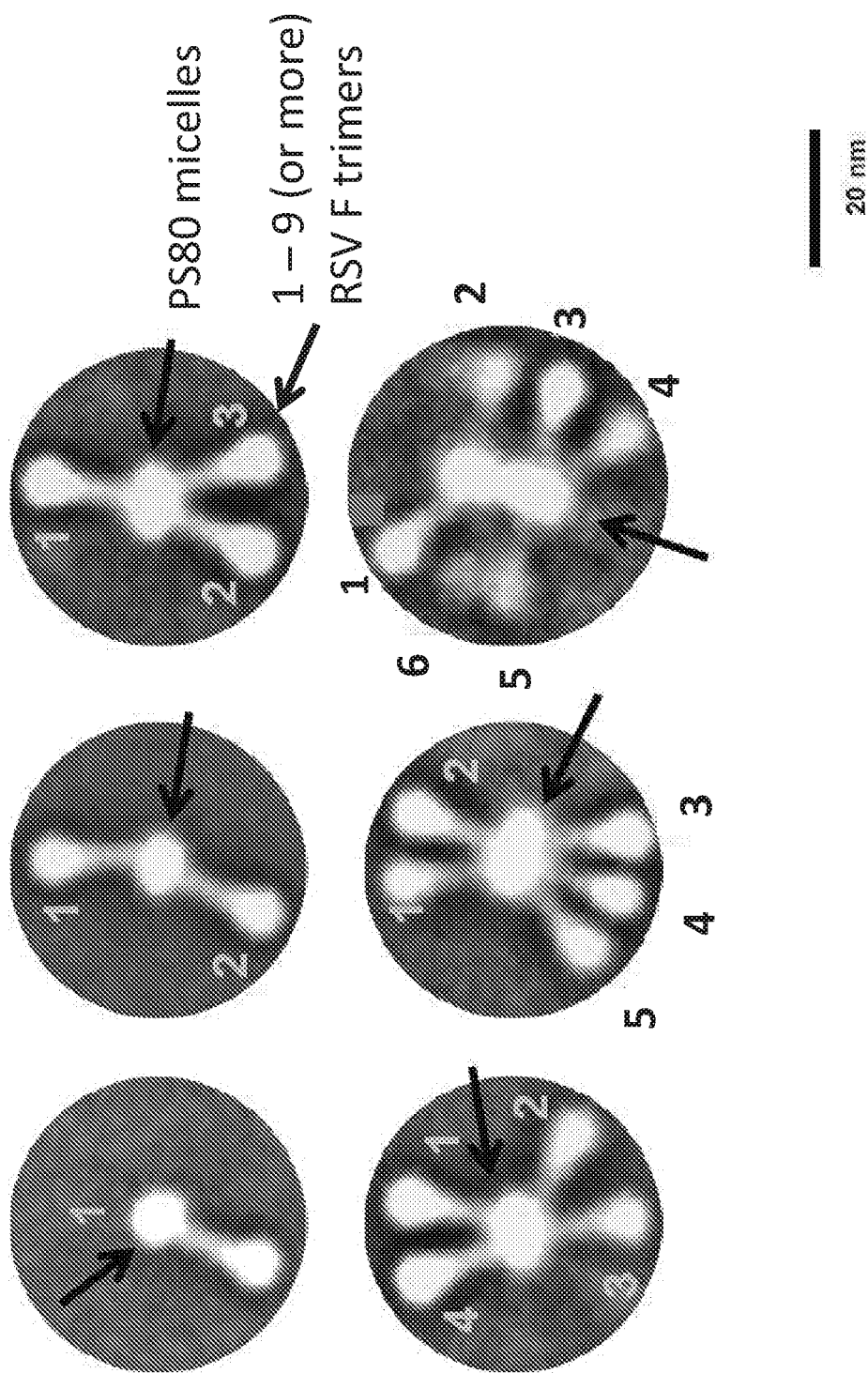
Fig. 2. RSV F Nanoparticles

Fig. 3. Analysis of Hospitalization for All-Cause* COPD Exacerbations

| E301 Day 0-182 | Placebo | Vaccine | VE% | 95% CI | p value |
|---|---|---|---|---|---|
| COPD hospitalization rate in all subjects | 23/5935 (0.39%) | 9/5921 (0.15%) | 60.8% | 15.2—81.9 | 0.017 |
| COPD hospitalization rate in subjects with baseline COPD | 15/362 (4.1%) | 9/403 (2.2%) | 46.1% | -23—76.4 | 0.14 |
| E 201 Day 0-182 | | | | | |
| COPD hospitalization rate in all subjects | 4/801 (0.50%) | 0/798 (0%) | 100% | NC | NC |
| COPD hospitalization rate in subjects with baseline COPD | 2/62 (3.2%) | 0/58 (0%) | 100% | NC | NC |

*Not associated with RSV detection

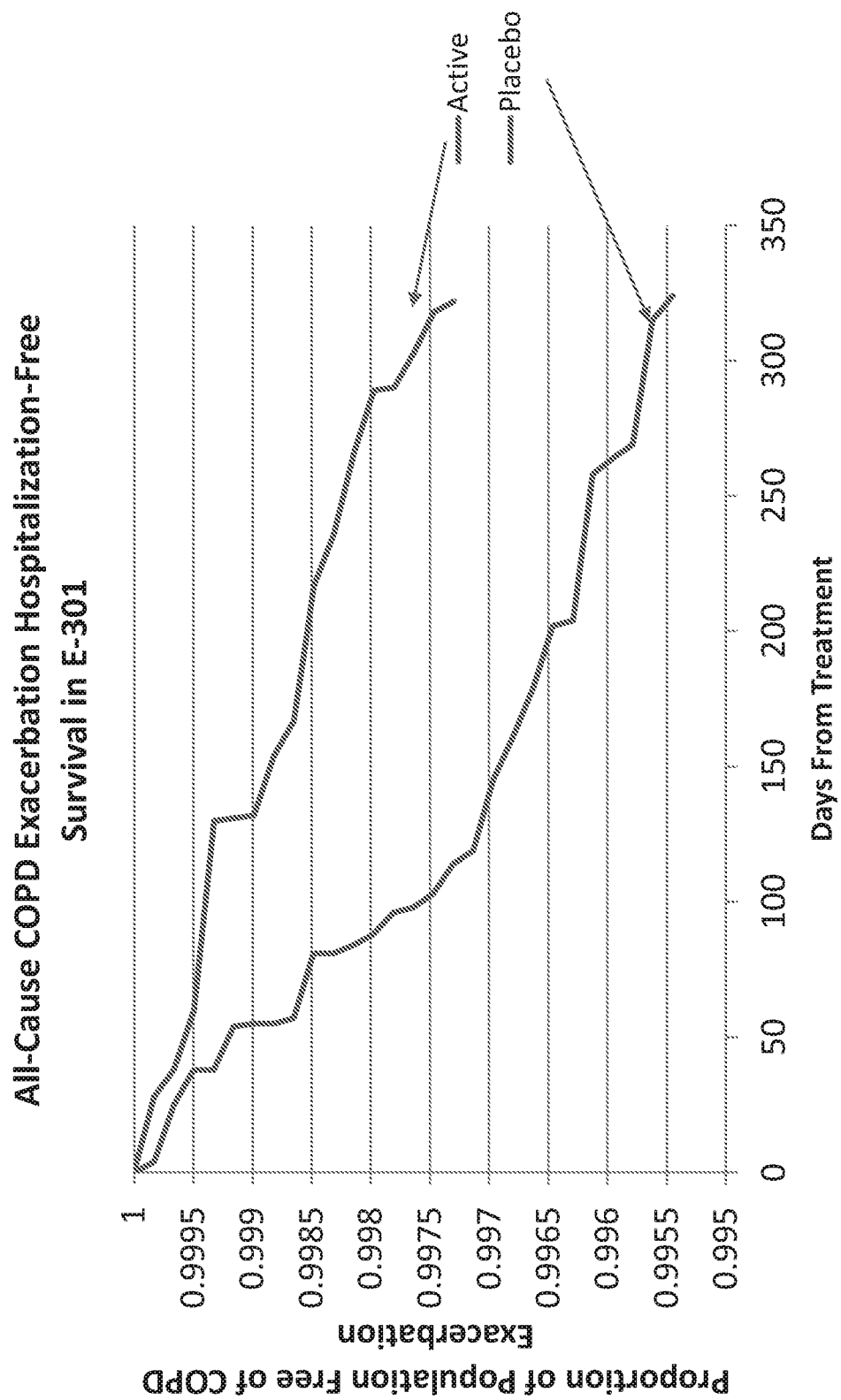
Fig. 4. COPD Hospitalizations in E-301

SEQUENCE LISTING

<160> NUMBER OF SEQ ID NOS: 20

<210> SEQ ID NO 1

-continued

```
<211> LENGTH: 1725
<212> TYPE: DNA
<213> ORGANISM: Respiratory syncytial virus

<400> SEQUENCE: 1
atggagttgc taatcctcaa agcaaatgca attaccacaa tcctcactgc agtcacattt      60
tgttttgctt ctggtcaaaa catcactgaa gaattttatc aatcaacatg cagtgcagtt     120
agcaaaggct atcttagtgc tctgagaact ggttggtata ccagtgttat aactatagaa     180
ttaagtaata tcaaggaaaa taagtgtaat ggaacagatg ctaaggtaaa attgataaaa     240
caagaattag ataaatataa aaatgctgta acagaattgc agttgctcat gcaaagcaca     300
ccaccaacaa acaatcgagc cagaagagaa ctaccaaggt ttatgaatta tacactcaac     360
aatgccaaaa aaccaatgt aacattaagc aagaaaagga aagaagatt tcttggtttt     420 ttgttaggtg ttggatctgc aatcgccagt ggcgttgctg tatctaaggt cctgcaccta     480
gaaggggaag tgaacaagat caaaagtgct ctactatcca caaacaaggc tgtagtcagc     540
ttatcaaatg gagttagtgt cttaaccagc aaagtgttag acctcaaaaa ctatatagat     600
aaacaattgt tacctattgt gaacaagcaa agctgcagca tatcaaatat agaaactgtg     660
atagagttcc aacaaaagaa caacagacta ctagagatta ccaggaatt tagtgttaat     720 gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtcc ataataaaag aggaagtctt agcatatgta     900
gtacaattac cactatatgg tgttatagat acaccctgtt ggaaactaca cacatcccct     960
ctatgtacaa ccaacacaaa agaagggtcc aacatctgtt taacaagaac tgacagagga    1020
tggtactgtg acaatgcagg atcagtatct ttcttcccac aagctgaaac atgtaaagtt    1080
caatcaaatc gagtattttg tgacacaatg aacagtttaa cattaccaag tgaaataaat    1140
ctctgcaatt tgacatatt caaccccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga catttctaa cgggtgcgat    1320 tatgtatcaa ataaagggat ggacactgtg tctgtaggta acacattata ttatgtaaat    1380
aagcaagaag gtaaaagtct ctatgtaaaa ggtgaaccaa taataaattt ctatgaccca    1440
ttagtattcc cctctgatga atttgatgca tcaatatctc aagtcaacga aagattaac     1500 cagagcctag catttattcg taaatccgat gaattattac ataatgtaaa tgctggtaaa    1560
tccaccacaa atatcatgat aactactata attatagtga ttatagtaat attgttatca    1620
ttaattgctg ttggactgct cttatactgt aaggccagaa gcacaccagt cacactaagc    1680
aaagatcaac tgagtggtat aaataatatt gcatttagta actaa                    1725

<210> SEQ ID NO 2
<211> LENGTH: 574
<212> TYPE: PRT
<213> ORGANISM: Respiratory syncytial virus

<400> SEQUENCE: 2

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

```
            35                  40                  45
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Pro Thr Asn Asn Arg Ala Arg Arg Glu Leu Pro
                100                 105                 110

Arg Phe Met Asn Tyr Thr Leu Asn Asn Ala Lys Lys Thr Asn Val Thr
             115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
450                 455                 460
```

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 3
<211> LENGTH: 573
<212> TYPE: PRT
<213> ORGANISM: Artificial Sequence
<220> FEATURE:
<223> OTHER INFORMATION: Deletion of 137 (delta 1)

<400> SEQUENCE: 3

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Leu Gly Phe Leu Leu Gly Val Gly
    130                 135                 140

Ser Ala Ile Ala Ser Gly Val Ala Val Ser Lys Val Leu His Leu Glu
145                 150                 155                 160

Gly Glu Val Asn Lys Ile Lys Ser Ala Leu Leu Ser Thr Asn Lys Ala
                165                 170                 175

Val Val Ser Leu Ser Asn Gly Val Ser Val Leu Thr Ser Lys Val Leu
            180                 185                 190

Asp Leu Lys Asn Tyr Ile Asp Lys Gln Leu Leu Pro Ile Val Asn Lys
        195                 200                 205

Gln Ser Cys Ser Ile Ser Asn Ile Glu Thr Val Ile Glu Phe Gln Gln
    210                 215                 220

Lys Asn Asn Arg Leu Leu Glu Ile Thr Arg Glu Phe Ser Val Asn Ala
225                 230                 235                 240

Gly Val Thr Thr Pro Val Ser Thr Tyr Met Leu Thr Asn Ser Glu Leu
                245                 250                 255
```

```
Leu Ser Leu Ile Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
            275                 280                 285

Ser Ile Ile Lys Glu Glu Val Leu Ala Tyr Val Val Gln Leu Pro Leu
            290                 295                 300

Tyr Gly Val Ile Asp Thr Pro Cys Trp Lys Leu His Thr Ser Pro Leu
305                 310                 315                 320

Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
            355                 360                 365

Met Asn Ser Leu Thr Leu Pro Ser Glu Val Asn Leu Cys Asn Val Asp
            370                 375                 380

Ile Phe Asn Pro Lys Tyr Asp Cys Lys Ile Met Thr Ser Lys Thr Asp
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
            435                 440                 445

Val Ser Val Gly Asn Thr Leu Tyr Tyr Val Asn Lys Gln Glu Gly Lys
            450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
            485                 490                 495

Lys Ile Asn Gln Ser Leu Ala Phe Ile Arg Lys Ser Asp Glu Leu Leu
            500                 505                 510

His Asn Val Asn Ala Gly Lys Ser Thr Thr Asn Ile Met Ile Thr Thr
            515                 520                 525

Ile Ile Ile Val Ile Ile Val Ile Leu Leu Ser Leu Ile Ala Val Gly
            530                 535                 540

Leu Leu Leu Tyr Cys Lys Ala Arg Ser Thr Pro Val Thr Leu Ser Lys
545                 550                 555                 560

Asp Gln Leu Ser Gly Ile Asn Asn Ile Ala Phe Ser Asn
                565                 570

<210> SEQ ID NO 4
<211> LENGTH: 572
<212> TYPE: PRT
<213> ORGANISM: Artificial Sequence
<220> FEATURE:
<223> OTHER INFORMATION: Deletion of 137-138 (delta 2)

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45
```

```
Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Gly Phe Leu Leu Gly Val Gly Ser
130                 135                 140

Ala Ile Ala Ser Gly Val Ala Val Ser Lys Val Leu His Leu Glu Gly
145                 150                 155                 160

Glu Val Asn Lys Ile Lys Ser Ala Leu Leu Ser Thr Asn Lys Ala Val
                165                 170                 175

Val Ser Leu Ser Asn Gly Val Ser Val Leu Thr Ser Lys Val Leu Asp
            180                 185                 190

Leu Lys Asn Tyr Ile Asp Lys Gln Leu Leu Pro Ile Val Asn Lys Gln
        195                 200                 205

Ser Cys Ser Ile Ser Asn Ile Glu Thr Val Ile Glu Phe Gln Gln Lys
210                 215                 220

Asn Asn Arg Leu Leu Glu Ile Thr Arg Glu Phe Ser Val Asn Ala Gly
225                 230                 235                 240

Val Thr Thr Pro Val Ser Thr Tyr Met Leu Thr Asn Ser Glu Leu Leu
                245                 250                 255

Ser Leu Ile Asn Asp Met Pro Ile Thr Asn Asp Gln Lys Lys Leu Met
            260                 265                 270

Ser Asn Asn Val Gln Ile Val Arg Gln Gln Ser Tyr Ser Ile Met Ser
        275                 280                 285

Ile Ile Lys Glu Glu Val Leu Ala Tyr Val Val Gln Leu Pro Leu Tyr
290                 295                 300

Gly Val Ile Asp Thr Pro Cys Trp Lys Leu His Thr Ser Pro Leu Cys
305                 310                 315                 320

Thr Thr Asn Thr Lys Glu Gly Ser Asn Ile Cys Leu Thr Arg Thr Asp
                325                 330                 335

Arg Gly Trp Tyr Cys Asp Asn Ala Gly Ser Val Ser Phe Phe Pro Gln
            340                 345                 350

Ala Glu Thr Cys Lys Val Gln Ser Asn Arg Val Phe Cys Asp Thr Met
        355                 360                 365

Asn Ser Leu Thr Leu Pro Ser Glu Val Asn Leu Cys Asn Val Asp Ile
370                 375                 380

Phe Asn Pro Lys Tyr Asp Cys Lys Ile Met Thr Ser Lys Thr Asp Val
385                 390                 395                 400

Ser Ser Ser Val Ile Thr Ser Leu Gly Ala Ile Val Ser Cys Tyr Gly
                405                 410                 415

Lys Thr Lys Cys Thr Ala Ser Asn Lys Asn Arg Gly Ile Ile Lys Thr
            420                 425                 430

Phe Ser Asn Gly Cys Asp Tyr Val Ser Asn Lys Gly Val Asp Thr Val
        435                 440                 445

Ser Val Gly Asn Thr Leu Tyr Tyr Val Asn Lys Gln Glu Gly Lys Ser
450                 455                 460
```

```
Leu Tyr Val Lys Gly Glu Pro Ile Ile Asn Phe Tyr Asp Pro Leu Val
465                 470                 475                 480

Phe Pro Ser Asp Glu Phe Asp Ala Ser Ile Ser Gln Val Asn Glu Lys
                485                 490                 495

Ile Asn Gln Ser Leu Ala Phe Ile Arg Lys Ser Asp Glu Leu Leu His
            500                 505                 510

Asn Val Asn Ala Gly Lys Ser Thr Thr Asn Ile Met Ile Thr Thr Ile
            515                 520                 525

Ile Ile Val Ile Ile Val Ile Leu Leu Ser Leu Ile Ala Val Gly Leu
        530                 535                 540

Leu Leu Tyr Cys Lys Ala Arg Ser Thr Pro Val Thr Leu Ser Lys Asp
545                 550                 555                 560

Gln Leu Ser Gly Ile Asn Asn Ile Ala Phe Ser Asn
                565                 570

<210> SEQ ID NO 5
<211> LENGTH: 571
<212> TYPE: PRT
<213> ORGANISM: Artificial Sequence
<220> FEATURE:
<223> OTHER INFORMATION: Deletion of 137-139 (delta 3)

<400> SEQUENCE: 5

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Phe Leu Leu Gly Val Gly Ser Ala
    130                 135                 140

Ile Ala Ser Gly Val Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175

Ser Leu Ser Asn Gly Val Ser Val Leu Thr Ser Lys Val Leu Asp Leu
            180                 185                 190

Lys Asn Tyr Ile Asp Lys Gln Leu Leu Pro Ile Val Asn Lys Gln Ser
        195                 200                 205

Cys Ser Ile Ser Asn Ile Glu Thr Val Ile Glu Phe Gln Gln Lys Asn
    210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255
```

```
Leu Ile Asn Asp Met Pro Ile Thr Asn Asp Gln Lys Lys Leu Met Ser
            260                 265                 270

Asn Asn Val Gln Ile Val Arg Gln Gln Ser Tyr Ser Ile Met Ser Ile
        275                 280                 285

Ile Lys Glu Glu Val Leu Ala Tyr Val Val Gln Leu Pro Leu Tyr Gly
    290                 295                 300

Val Ile Asp Thr Pro Cys Trp Lys Leu His Thr Ser Pro Leu Cys Thr
305                 310                 315                 320

Thr Asn Thr Lys Glu Gly Ser Asn Ile Cys Leu Thr Arg Thr Asp Arg
            325                 330                 335

Gly Trp Tyr Cys Asp Asn Ala Gly Ser Val Ser Phe Phe Pro Gln Ala
        340                 345                 350

Glu Thr Cys Lys Val Gln Ser Asn Arg Val Phe Cys Asp Thr Met Asn
    355                 360                 365

Ser Leu Thr Leu Pro Ser Glu Val Asn Leu Cys Asn Val Asp Ile Phe
370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
            405                 410                 415

Thr Lys Cys Thr Ala Ser Asn Lys Asn Arg Gly Ile Ile Lys Thr Phe
        420                 425                 430

Ser Asn Gly Cys Asp Tyr Val Ser Asn Lys Gly Val Asp Thr Val Ser
    435                 440                 445

Val Gly Asn Thr Leu Tyr Tyr Val Asn Lys Gln Glu Gly Lys Ser Leu
450                 455                 460

Tyr Val Lys Gly Glu Pro Ile Ile Asn Phe Tyr Asp Pro Leu Val Phe
465                 470                 475                 480

Pro Ser Asp Glu Phe Asp Ala Ser Ile Ser Gln Val Asn Glu Lys Ile
            485                 490                 495

Asn Gln Ser Leu Ala Phe Ile Arg Lys Ser Asp Glu Leu Leu His Asn
        500                 505                 510

Val Asn Ala Gly Lys Ser Thr Thr Asn Ile Met Ile Thr Thr Ile Ile
    515                 520                 525

Ile Val Ile Ile Val Ile Leu Leu Ser Leu Ile Ala Val Gly Leu Leu
530                 535                 540

Leu Tyr Cys Lys Ala Arg Ser Thr Pro Val Thr Leu Ser Lys Asp Gln
545                 550                 555                 560

Leu Ser Gly Ile Asn Asn Ile Ala Phe Ser Asn
            565                 570

<210> SEQ ID NO 6
<211> LENGTH: 570
<212> TYPE: PRT
<213> ORGANISM: Artificial Sequence
<220> FEATURE:
<223> OTHER INFORMATION: Deletion of 137-140 (delta 4)

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
    50              55              60

Lys Glu Asn Lys Cys Asn Gly Thr Asp Ala Lys Val Lys Leu Ile Lys
65              70              75              80

Gln Glu Leu Asp Lys Tyr Lys Asn Ala Val Thr Glu Leu Gln Leu Leu
                85              90              95

Met Gln Ser Thr Pro Ala Thr Asn Asn Arg Ala Arg Arg Glu Leu Pro
            100             105             110

Arg Phe Met Asn Tyr Thr Leu Asn Asn Ala Lys Lys Thr Asn Val Thr
        115             120             125

Leu Ser Lys Lys Gln Lys Gln Gln Leu Leu Gly Val Gly Ser Ala Ile
    130             135             140

Ala Ser Gly Val Ala Val Ser Lys Val Leu His Leu Glu Gly Glu Val
145             150             155             160

Asn Lys Ile Lys Ser Ala Leu Leu Ser Thr Asn Lys Ala Val Val Ser
                165             170             175

Leu Ser Asn Gly Val Ser Val Leu Thr Ser Lys Val Leu Asp Leu Lys
            180             185             190

Asn Tyr Ile Asp Lys Gln Leu Leu Pro Ile Val Asn Lys Gln Ser Cys
        195             200             205

Ser Ile Ser Asn Ile Glu Thr Val Ile Glu Phe Gln Gln Lys Asn Asn
    210             215             220

Arg Leu Leu Glu Ile Thr Arg Glu Phe Ser Val Asn Ala Gly Val Thr
225             230             235             240

Thr Pro Val Ser Thr Tyr Met Leu Thr Asn Ser Glu Leu Leu Ser Leu
                245             250             255

Ile Asn Asp Met Pro Ile Thr Asn Asp Gln Lys Lys Leu Met Ser Asn
            260             265             270

Asn Val Gln Ile Val Arg Gln Gln Ser Tyr Ser Ile Met Ser Ile Ile
        275             280             285

Lys Glu Glu Val Leu Ala Tyr Val Val Gln Leu Pro Leu Tyr Gly Val
    290             295             300

Ile Asp Thr Pro Cys Trp Lys Leu His Thr Ser Pro Leu Cys Thr Thr
305             310             315             320

Asn Thr Lys Glu Gly Ser Asn Ile Cys Leu Thr Arg Thr Asp Arg Gly
                325             330             335

Trp Tyr Cys Asp Asn Ala Gly Ser Val Ser Phe Phe Pro Gln Ala Glu
            340             345             350

Thr Cys Lys Val Gln Ser Asn Arg Val Phe Cys Asp Thr Met Asn Ser
        355             360             365

Leu Thr Leu Pro Ser Glu Val Asn Leu Cys Asn Val Asp Ile Phe Asn
    370             375             380

Pro Lys Tyr Asp Cys Lys Ile Met Thr Ser Lys Thr Asp Val Ser Ser
385             390             395             400

Ser Val Ile Thr Ser Leu Gly Ala Ile Val Ser Cys Tyr Gly Lys Thr
                405             410             415

Lys Cys Thr Ala Ser Asn Lys Asn Arg Gly Ile Ile Lys Thr Phe Ser
            420             425             430

Asn Gly Cys Asp Tyr Val Ser Asn Lys Gly Val Asp Thr Val Ser Val
        435             440             445

Gly Asn Thr Leu Tyr Tyr Val Asn Lys Gln Glu Gly Lys Ser Leu Tyr
    450             455             460

Val Lys Gly Glu Pro Ile Ile Asn Phe Tyr Asp Pro Leu Val Phe Pro
```

```
                465                 470                 475                 480
Ser Asp Glu Phe Asp Ala Ser Ile Ser Gln Val Asn Glu Lys Ile Asn
                    485                 490                 495

Gln Ser Leu Ala Phe Ile Arg Lys Ser Asp Glu Leu Leu His Asn Val
            500                 505                 510

Asn Ala Gly Lys Ser Thr Thr Asn Ile Met Ile Thr Thr Ile Ile Ile
            515                 520                 525

Val Ile Ile Val Ile Leu Leu Ser Leu Ile Ala Val Gly Leu Leu Leu
            530                 535                 540

Tyr Cys Lys Ala Arg Ser Thr Pro Val Thr Leu Ser Lys Asp Gln Leu
545                 550                 555                 560

Ser Gly Ile Asn Asn Ile Ala Phe Ser Asn
                565                 570

<210> SEQ ID NO 7
<211> LENGTH: 569
<212> TYPE: PRT
<213> ORGANISM: Artificial Sequence
<220> FEATURE:
<223> OTHER INFORMATION: Deletion of 137-141 (delta 5)

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Leu Gly Val Gly Ser Ala Ile Ala
130                 135                 140

Ser Gly Val Ala Val Ser Lys Val Leu His Leu Glu Gly Glu Val Asn
145                 150                 155                 160

Lys Ile Lys Ser Ala Leu Leu Ser Thr Asn Lys Ala Val Val Ser Leu
                165                 170                 175

Ser Asn Gly Val Ser Val Leu Thr Ser Lys Val Leu Asp Leu Lys Asn
            180                 185                 190

Tyr Ile Asp Lys Gln Leu Leu Pro Ile Val Asn Lys Gln Ser Cys Ser
        195                 200                 205

Ile Ser Asn Ile Glu Thr Val Ile Glu Phe Gln Gln Lys Asn Asn Arg
    210                 215                 220

Leu Leu Glu Ile Thr Arg Glu Phe Ser Val Asn Ala Gly Val Thr Thr
225                 230                 235                 240

Pro Val Ser Thr Tyr Met Leu Thr Asn Ser Glu Leu Leu Ser Leu Ile
                245                 250                 255

Asn Asp Met Pro Ile Thr Asn Asp Gln Lys Lys Leu Met Ser Asn Asn
```

```
            260                 265                 270
Val Gln Ile Val Arg Gln Ser Tyr Ser Ile Met Ser Ile Ile Lys
        275                 280                 285
Glu Glu Val Leu Ala Tyr Val Gln Leu Pro Leu Tyr Gly Val Ile
        290                 295                 300
Asp Thr Pro Cys Trp Lys Leu His Thr Ser Pro Leu Cys Thr Thr Asn
305                 310                 315                 320
Thr Lys Glu Gly Ser Asn Ile Cys Leu Thr Arg Thr Asp Arg Gly Trp
            325                 330                 335
Tyr Cys Asp Asn Ala Gly Ser Val Ser Phe Phe Pro Gln Ala Glu Thr
            340                 345                 350
Cys Lys Val Gln Ser Asn Arg Val Phe Cys Asp Thr Met Asn Ser Leu
        355                 360                 365
Thr Leu Pro Ser Glu Val Asn Leu Cys Asn Val Asp Ile Phe Asn Pro
        370                 375                 380
Lys Tyr Asp Cys Lys Ile Met Thr Ser Lys Thr Asp Val Ser Ser Ser
385                 390                 395                 400
Val Ile Thr Ser Leu Gly Ala Ile Val Ser Cys Tyr Gly Lys Thr Lys
            405                 410                 415
Cys Thr Ala Ser Asn Lys Asn Arg Gly Ile Ile Lys Thr Phe Ser Asn
            420                 425                 430
Gly Cys Asp Tyr Val Ser Asn Lys Gly Val Asp Thr Val Ser Val Gly
            435                 440                 445
Asn Thr Leu Tyr Tyr Val Asn Lys Gln Glu Gly Lys Ser Leu Tyr Val
        450                 455                 460
Lys Gly Glu Pro Ile Ile Asn Phe Tyr Asp Pro Leu Val Phe Pro Ser
465                 470                 475                 480
Asp Glu Phe Asp Ala Ser Ile Ser Gln Val Asn Glu Lys Ile Asn Gln
            485                 490                 495
Ser Leu Ala Phe Ile Arg Lys Ser Asp Glu Leu Leu His Asn Val Asn
        500                 505                 510
Ala Gly Lys Ser Thr Thr Asn Ile Met Ile Thr Thr Ile Ile Ile Val
            515                 520                 525
Ile Ile Val Ile Leu Leu Ser Leu Ile Ala Val Gly Leu Leu Leu Tyr
        530                 535                 540
Cys Lys Ala Arg Ser Thr Pro Val Thr Leu Ser Lys Asp Gln Leu Ser
545                 550                 555                 560
Gly Ile Asn Asn Ile Ala Phe Ser Asn
                565

<210> SEQ ID NO 8
<211> LENGTH: 564
<212> TYPE: PRT
<213> ORGANISM: Artificial Sequence
<220> FEATURE:
<223> OTHER INFORMATION: Deletion of 137-146 (delta 10)

<400> SEQUENCE: 8

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
```

```
                50                  55                  60
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Gln Lys Gln Gln Ala Ile Ala Ser Gly Val Ala Val
                130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
                180                 185                 190

Leu Leu Pro Ile Val Asn Lys Gln Ser Cys Ser Ile Ser Asn Ile Glu
                195                 200                 205

Thr Val Ile Glu Phe Gln Gln Lys Asn Asn Arg Leu Leu Glu Ile Thr
                210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
                260                 265                 270

Gln Gln Ser Tyr Ser Ile Met Ser Ile Ile Lys Glu Glu Val Leu Ala
                275                 280                 285

Tyr Val Val Gln Leu Pro Leu Tyr Gly Val Ile Asp Thr Pro Cys Trp
                290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
                340                 345                 350

Asn Arg Val Phe Cys Asp Thr Met Asn Ser Leu Thr Leu Pro Ser Glu
                355                 360                 365

Val Asn Leu Cys Asn Val Asp Ile Phe Asn Pro Lys Tyr Asp Cys Lys
                370                 375                 380

Ile Met Thr Ser Lys Thr Asp Val Ser Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
                420                 425                 430

Ser Asn Lys Gly Val Asp Thr Val Ser Val Gly Asn Thr Leu Tyr Tyr
                435                 440                 445

Val Asn Lys Gln Glu Gly Lys Ser Leu Tyr Val Lys Gly Glu Pro Ile
                450                 455                 460

Ile Asn Phe Tyr Asp Pro Leu Val Phe Pro Ser Asp Glu Phe Asp Ala
465                 470                 475                 480
```

```
Ser Ile Ser Gln Val Asn Glu Lys Ile Asn Gln Ser Leu Ala Phe Ile
            485                 490                 495

Arg Lys Ser Asp Glu Leu Leu His Asn Val Asn Ala Gly Lys Ser Thr
            500                 505                 510

Thr Asn Ile Met Ile Thr Thr Ile Ile Val Ile Ile Val Ile Leu
            515                 520                 525

Leu Ser Leu Ile Ala Val Gly Leu Leu Leu Tyr Cys Lys Ala Arg Ser
            530                 535                 540

Thr Pro Val Thr Leu Ser Lys Asp Gln Leu Ser Gly Ile Asn Asn Ile
545                 550                 555                 560

Ala Phe Ser Asn

<210> SEQ ID NO 9
<211> LENGTH: 568
<212> TYPE: PRT
<213> ORGANISM: Artificial Sequence
<220> FEATURE:
<223> OTHER INFORMATION: Deletion of 137-142 (delta 6)

<400> SEQUENCE: 9

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Gly Val Gly Ser Ala Ile Ala Ser
130                 135                 140

Gly Val Ala Val Ser Lys Val Leu His Leu Glu Gly Glu Val Asn Lys
145                 150                 155                 160

Ile Lys Ser Ala Leu Leu Ser Thr Asn Lys Ala Val Val Ser Leu Ser
            165                 170                 175

Asn Gly Val Ser Val Leu Thr Ser Lys Val Leu Asp Leu Lys Asn Tyr
            180                 185                 190

Ile Asp Lys Gln Leu Leu Pro Ile Val Asn Lys Gln Ser Cys Ser Ile
            195                 200                 205

Ser Asn Ile Glu Thr Val Ile Glu Phe Gln Gln Lys Asn Asn Arg Leu
            210                 215                 220

Leu Glu Ile Thr Arg Glu Phe Ser Val Asn Ala Gly Val Thr Thr Pro
225                 230                 235                 240

Val Ser Thr Tyr Met Leu Thr Asn Ser Glu Leu Leu Ser Leu Ile Asn
                245                 250                 255

Asp Met Pro Ile Thr Asn Asp Gln Lys Lys Leu Met Ser Asn Asn Val
            260                 265                 270
```

-continued

```
Gln Ile Val Arg Gln Gln Ser Tyr Ser Ile Met Ser Ile Lys Glu
            275                 280                 285

Glu Val Leu Ala Tyr Val Val Gln Leu Pro Leu Tyr Gly Val Ile Asp
        290                 295                 300

Thr Pro Cys Trp Lys Leu His Thr Ser Pro Leu Cys Thr Thr Asn Thr
305                 310                 315                 320

Lys Glu Gly Ser Asn Ile Cys Leu Thr Arg Thr Asp Arg Gly Trp Tyr
                325                 330                 335

Cys Asp Asn Ala Gly Ser Val Ser Phe Phe Pro Gln Ala Glu Thr Cys
                340                 345                 350

Lys Val Gln Ser Asn Arg Val Phe Cys Asp Thr Met Asn Ser Leu Thr
            355                 360                 365

Leu Pro Ser Glu Val Asn Leu Cys Asn Val Asp Ile Phe Asn Pro Lys
        370                 375                 380

Tyr Asp Cys Lys Ile Met Thr Ser Lys Thr Asp Val Ser Ser Ser Val
385                 390                 395                 400

Ile Thr Ser Leu Gly Ala Ile Val Ser Cys Tyr Gly Lys Thr Lys Cys
                405                 410                 415

Thr Ala Ser Asn Lys Asn Arg Gly Ile Ile Lys Thr Phe Ser Asn Gly
                420                 425                 430

Cys Asp Tyr Val Ser Asn Lys Gly Val Asp Thr Val Ser Val Gly Asn
            435                 440                 445

Thr Leu Tyr Tyr Val Asn Lys Gln Glu Gly Lys Ser Leu Tyr Val Lys
        450                 455                 460

Gly Glu Pro Ile Ile Asn Phe Tyr Asp Pro Leu Val Phe Pro Ser Asp
465                 470                 475                 480

Glu Phe Asp Ala Ser Ile Ser Gln Val Asn Glu Lys Ile Asn Gln Ser
                485                 490                 495

Leu Ala Phe Ile Arg Lys Ser Asp Glu Leu Leu His Asn Val Asn Ala
                500                 505                 510

Gly Lys Ser Thr Thr Asn Ile Met Ile Thr Thr Ile Ile Ile Val Ile
            515                 520                 525

Ile Val Ile Leu Leu Ser Leu Ile Ala Val Gly Leu Leu Leu Tyr Cys
        530                 535                 540

Lys Ala Arg Ser Thr Pro Val Thr Leu Ser Lys Asp Gln Leu Ser Gly
545                 550                 555                 560

Ile Asn Asn Ile Ala Phe Ser Asn
                565
```

```
<210> SEQ ID NO 10
<211> LENGTH: 567
<212> TYPE: PRT
<213> ORGANISM: Artificial Sequence
<220> FEATURE:
<223> OTHER INFORMATION: Deletion of 137-143 (delta 7)

<400> SEQUENCE: 10
```

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Gln Lys Gln Gln Val Gly Ser Ala Ile Ala Ser Gly
    130                 135                 140

Val Ala Val Ser Lys Val Leu His Leu Glu Gly Glu Val Asn Lys Ile
145                 150                 155                 160

Lys Ser Ala Leu Leu Ser Thr Asn Lys Ala Val Val Ser Leu Ser Asn
            165                 170                 175

Gly Val Ser Val Leu Thr Ser Lys Val Leu Asp Leu Lys Asn Tyr Ile
            180                 185                 190

Asp Lys Gln Leu Leu Pro Ile Val Asn Lys Gln Ser Cys Ser Ile Ser
    195                 200                 205

Asn Ile Glu Thr Val Ile Glu Phe Gln Gln Lys Asn Asn Arg Leu Leu
    210                 215                 220

Glu Ile Thr Arg Glu Phe Ser Val Asn Ala Gly Val Thr Thr Pro Val
225                 230                 235                 240

Ser Thr Tyr Met Leu Thr Asn Ser Glu Leu Leu Ser Leu Ile Asn Asp
            245                 250                 255

Met Pro Ile Thr Asn Asp Gln Lys Lys Leu Met Ser Asn Asn Val Gln
            260                 265                 270

Ile Val Arg Gln Gln Ser Tyr Ser Ile Met Ser Ile Ile Lys Glu Glu
    275                 280                 285

Val Leu Ala Tyr Val Val Gln Leu Pro Leu Tyr Gly Val Ile Asp Thr
            290                 295                 300

Pro Cys Trp Lys Leu His Thr Ser Pro Leu Cys Thr Thr Asn Thr Lys
305                 310                 315                 320

Glu Gly Ser Asn Ile Cys Leu Thr Arg Thr Asp Arg Gly Trp Tyr Cys
            325                 330                 335

Asp Asn Ala Gly Ser Val Ser Phe Phe Pro Gln Ala Glu Thr Cys Lys
            340                 345                 350

Val Gln Ser Asn Arg Val Phe Cys Asp Thr Met Asn Ser Leu Thr Leu
    355                 360                 365

Pro Ser Glu Val Asn Leu Cys Asn Val Asp Ile Phe Asn Pro Lys Tyr
    370                 375                 380

Asp Cys Lys Ile Met Thr Ser Lys Thr Asp Val Ser Ser Ser Val Ile
385                 390                 395                 400

Thr Ser Leu Gly Ala Ile Val Ser Cys Tyr Gly Lys Thr Lys Cys Thr
            405                 410                 415

Ala Ser Asn Lys Asn Arg Gly Ile Ile Lys Thr Phe Ser Asn Gly Cys
            420                 425                 430

Asp Tyr Val Ser Asn Lys Gly Val Asp Thr Val Ser Val Gly Asn Thr
    435                 440                 445

Leu Tyr Tyr Val Asn Lys Gln Glu Gly Lys Ser Leu Tyr Val Lys Gly
    450                 455                 460

Glu Pro Ile Ile Asn Phe Tyr Asp Pro Leu Val Phe Pro Ser Asp Glu
465                 470                 475                 480

Phe Asp Ala Ser Ile Ser Gln Val Asn Glu Lys Ile Asn Gln Ser Leu

```
                        485                 490                 495
Ala Phe Ile Arg Lys Ser Asp Glu Leu Leu His Asn Val Asn Ala Gly
                500                 505                 510

Lys Ser Thr Thr Asn Ile Met Ile Thr Thr Ile Ile Val Ile Ile
            515                 520                 525

Val Ile Leu Leu Ser Leu Ile Ala Val Gly Leu Leu Tyr Cys Lys
        530                 535                 540

Ala Arg Ser Thr Pro Val Thr Leu Ser Lys Asp Gln Leu Ser Gly Ile
545                 550                 555                 560

Asn Asn Ile Ala Phe Ser Asn
                565

<210> SEQ ID NO 11
<211> LENGTH: 566
<212> TYPE: PRT
<213> ORGANISM: Artificial Sequence
<220> FEATURE:
<223> OTHER INFORMATION: Deletion of 137-144 (delta 8)

<400> SEQUENCE: 11

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gly Ser Ala Ile Ala Ser Gly Val
    130                 135                 140

Ala Val Ser Lys Val Leu His Leu Glu Gly Glu Val Asn Lys Ile Lys
145                 150                 155                 160

Ser Ala Leu Leu Ser Thr Asn Lys Ala Val Val Ser Leu Ser Asn Gly
                165                 170                 175

Val Ser Val Leu Thr Ser Lys Val Leu Asp Leu Lys Asn Tyr Ile Asp
            180                 185                 190

Lys Gln Leu Leu Pro Ile Val Asn Lys Gln Ser Cys Ser Ile Ser Asn
        195                 200                 205

Ile Glu Thr Val Ile Glu Phe Gln Gln Lys Asn Asn Arg Leu Leu Glu
    210                 215                 220

Ile Thr Arg Glu Phe Ser Val Asn Ala Gly Val Thr Thr Pro Val Ser
225                 230                 235                 240

Thr Tyr Met Leu Thr Asn Ser Glu Leu Leu Ser Leu Ile Asn Asp Met
                245                 250                 255

Pro Ile Thr Asn Asp Gln Lys Lys Leu Met Ser Asn Asn Val Gln Ile
            260                 265                 270

Val Arg Gln Gln Ser Tyr Ser Ile Met Ser Ile Ile Lys Glu Glu Val
```

```
            275                 280                 285
Leu Ala Tyr Val Val Gln Leu Pro Leu Tyr Gly Val Ile Asp Thr Pro
            290                 295                 300
Cys Trp Lys Leu His Thr Ser Pro Leu Cys Thr Thr Asn Thr Lys Glu
305                 310                 315                 320
Gly Ser Asn Ile Cys Leu Thr Arg Thr Asp Arg Gly Trp Tyr Cys Asp
                325                 330                 335
Asn Ala Gly Ser Val Ser Phe Phe Pro Gln Ala Glu Thr Cys Lys Val
                340                 345                 350
Gln Ser Asn Arg Val Phe Cys Asp Thr Met Asn Ser Leu Thr Leu Pro
            355                 360                 365
Ser Glu Val Asn Leu Cys Asn Val Asp Ile Phe Asn Pro Lys Tyr Asp
            370                 375                 380
Cys Lys Ile Met Thr Ser Lys Thr Asp Val Ser Ser Val Ile Thr
385                 390                 395                 400
Ser Leu Gly Ala Ile Val Ser Cys Tyr Gly Lys Thr Lys Cys Thr Ala
                405                 410                 415
Ser Asn Lys Asn Arg Gly Ile Ile Lys Thr Phe Ser Asn Gly Cys Asp
            420                 425                 430
Tyr Val Ser Asn Lys Gly Val Asp Thr Val Ser Val Gly Asn Thr Leu
            435                 440                 445
Tyr Tyr Val Asn Lys Gln Glu Gly Lys Ser Leu Tyr Val Lys Gly Glu
            450                 455                 460
Pro Ile Ile Asn Phe Tyr Asp Pro Leu Val Phe Pro Ser Asp Glu Phe
465                 470                 475                 480
Asp Ala Ser Ile Ser Gln Val Asn Glu Lys Ile Asn Gln Ser Leu Ala
                485                 490                 495
Phe Ile Arg Lys Ser Asp Glu Leu Leu His Asn Val Asn Ala Gly Lys
            500                 505                 510
Ser Thr Thr Asn Ile Met Ile Thr Thr Ile Ile Val Ile Ile Val
            515                 520                 525
Ile Leu Leu Ser Leu Ile Ala Val Gly Leu Leu Leu Tyr Cys Lys Ala
            530                 535                 540
Arg Ser Thr Pro Val Thr Leu Ser Lys Asp Gln Leu Ser Gly Ile Asn
545                 550                 555                 560
Asn Ile Ala Phe Ser Asn
            565

<210> SEQ ID NO 12
<211> LENGTH: 565
<212> TYPE: PRT
<213> ORGANISM: Artificial Sequence
<220> FEATURE:
<223> OTHER INFORMATION: Deletion of 137-145 (delta 9)

<400> SEQUENCE: 12

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
                20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
        50                  55                  60
Lys Glu Asn Lys Cys Asn Gly Thr Asp Ala Lys Val Lys Leu Ile Lys
```

```
            65                  70                  75                  80
Gln Glu Leu Asp Lys Tyr Lys Asn Ala Val Thr Glu Leu Gln Leu Leu
                    85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Gln Lys Gln Gln Ser Ala Ile Ala Ser Gly Val Ala
            130                 135                 140

Val Ser Lys Val Leu His Leu Glu Gly Glu Val Asn Lys Ile Lys Ser
145                 150                 155                 160

Ala Leu Leu Ser Thr Asn Lys Ala Val Val Ser Leu Ser Asn Gly Val
                165                 170                 175

Ser Val Leu Thr Ser Lys Val Leu Asp Leu Lys Asn Tyr Ile Asp Lys
                180                 185                 190

Gln Leu Leu Pro Ile Val Asn Lys Gln Ser Cys Ser Ile Ser Asn Ile
            195                 200                 205

Glu Thr Val Ile Glu Phe Gln Gln Lys Asn Asn Arg Leu Leu Glu Ile
        210                 215                 220

Thr Arg Glu Phe Ser Val Asn Ala Gly Val Thr Thr Pro Val Ser Thr
225                 230                 235                 240

Tyr Met Leu Thr Asn Ser Glu Leu Leu Ser Leu Ile Asn Asp Met Pro
                245                 250                 255

Ile Thr Asn Asp Gln Lys Lys Leu Met Ser Asn Asn Val Gln Ile Val
                260                 265                 270

Arg Gln Gln Ser Tyr Ser Ile Met Ser Ile Ile Lys Glu Glu Val Leu
            275                 280                 285

Ala Tyr Val Val Gln Leu Pro Leu Tyr Gly Val Ile Asp Thr Pro Cys
        290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
                340                 345                 350

Ser Asn Arg Val Phe Cys Asp Thr Met Asn Ser Leu Thr Leu Pro Ser
            355                 360                 365

Glu Val Asn Leu Cys Asn Val Asp Ile Phe Asn Pro Lys Tyr Asp Cys
        370                 375                 380

Lys Ile Met Thr Ser Lys Thr Asp Val Ser Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
        450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495
```

```
Ile Arg Lys Ser Asp Glu Leu Leu His Asn Val Asn Ala Gly Lys Ser
            500                 505                 510
Thr Thr Asn Ile Met Ile Thr Thr Ile Ile Val Ile Thr Ile Val Ile
            515                 520                 525
Leu Leu Ser Leu Ile Ala Val Gly Leu Leu Tyr Cys Lys Ala Arg
            530                 535                 540
Ser Thr Pro Val Thr Leu Ser Lys Asp Gln Leu Ser Gly Ile Asn Asn
545                 550                 555                 560
Ile Ala Phe Ser Asn
                565

<210> SEQ ID NO 13
<211> LENGTH: 565
<212> TYPE: PRT
<213> ORGANISM: Artificial Sequence
<220> FEATURE:
<223> OTHER INFORMATION: Deletion of 137-145 (delta 9) with wild type
      fusion cleavage site

<400> SEQUENCE: 13

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
                20                  25                  30
Tyr Gln Ser Thr Cys Ser Ala Val Ser Lys Gly Tyr Leu Ser Ala Leu
            35                  40                  45
Arg Thr Gly Trp Tyr Thr Ser Val Ile Thr Ile Glu Leu Ser Asn Ile
    50                  55                  60
Lys Glu Asn Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Ser Ala Ile Ala Ser Gly Val Ala
    130                 135                 140
Val Ser Lys Val Leu His Leu Glu Gly Glu Val Asn Lys Ile Lys Ser
145                 150                 155                 160
Ala Leu Leu Ser Thr Asn Lys Ala Val Val Ser Leu Ser Asn Gly Val
                165                 170                 175
Ser Val Leu Thr Ser Lys Val Leu Asp Leu Lys Asn Tyr Ile Asp Lys
            180                 185                 190
Gln Leu Leu Pro Ile Val Asn Lys Gln Ser Cys Ser Ile Ser Asn Ile
        195                 200                 205
Glu Thr Val Ile Glu Phe Gln Gln Lys Asn Asn Arg Leu Leu Glu Ile
    210                 215                 220
Thr Arg Glu Phe Ser Val Asn Ala Gly Val Thr Thr Pro Val Ser Thr
225                 230                 235                 240
Tyr Met Leu Thr Asn Ser Glu Leu Leu Ser Leu Ile Asn Asp Met Pro
                245                 250                 255
Ile Thr Asn Asp Gln Lys Lys Leu Met Ser Asn Asn Val Gln Ile Val
            260                 265                 270
Arg Gln Gln Ser Tyr Ser Ile Met Ser Ile Ile Lys Glu Glu Val Leu
```

```
            275                 280                 285
Ala Tyr Val Val Gln Leu Pro Leu Tyr Gly Val Ile Asp Thr Pro Cys
290                 295                 300

Trp Lys Leu His Thr Ser Pro Leu Cys Thr Thr Asn Thr Lys Glu Gly
305                 310                 315                 320

Ser Asn Ile Cys Leu Thr Arg Thr Asp Arg Gly Trp Tyr Cys Asp Asn
                325                 330                 335

Ala Gly Ser Val Ser Phe Phe Pro Gln Ala Glu Thr Cys Lys Val Gln
            340                 345                 350

Ser Asn Arg Val Phe Cys Asp Thr Met Asn Ser Leu Thr Leu Pro Ser
        355                 360                 365

Glu Val Asn Leu Cys Asn Val Asp Ile Phe Asn Pro Lys Tyr Asp Cys
370                 375                 380

Lys Ile Met Thr Ser Lys Thr Asp Val Ser Ser Val Ile Thr Ser
385                 390                 395                 400

Leu Gly Ala Ile Val Ser Cys Tyr Gly Lys Thr Lys Cys Thr Ala Ser
                405                 410                 415

Asn Lys Asn Arg Gly Ile Ile Lys Thr Phe Ser Asn Gly Cys Asp Tyr
            420                 425                 430

Val Ser Asn Lys Gly Val Asp Thr Val Ser Val Gly Asn Thr Leu Tyr
        435                 440                 445

Tyr Val Asn Lys Gln Glu Gly Lys Ser Leu Tyr Val Lys Gly Glu Pro
    450                 455                 460

Ile Ile Asn Phe Tyr Asp Pro Leu Val Phe Pro Ser Asp Glu Phe Asp
465                 470                 475                 480

Ala Ser Ile Ser Gln Val Asn Glu Lys Ile Asn Gln Ser Leu Ala Phe
                485                 490                 495

Ile Arg Lys Ser Asp Glu Leu Leu His Asn Val Asn Ala Gly Lys Ser
            500                 505                 510

Thr Thr Asn Ile Met Ile Thr Thr Ile Ile Val Ile Ile Val Ile
        515                 520                 525

Leu Leu Ser Leu Ile Ala Val Gly Leu Leu Leu Tyr Cys Lys Ala Arg
    530                 535                 540

Ser Thr Pro Val Thr Leu Ser Lys Asp Gln Leu Ser Gly Ile Asn Asn
545                 550                 555                 560

Ile Ala Phe Ser Asn
                565

<210> SEQ ID NO 14
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 14

Lys Lys Gln Lys Gln Gln
1               5

<210> SEQ ID NO 15
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 15
```

```
Gln Lys Gln Lys Gln Gln
1               5
```

<210> SEQ ID NO 16
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 16

```
Lys Lys Gln Lys Arg Gln
1               5
```

<210> SEQ ID NO 17
<211> LENGTH: 6
<212> TYPE: PRT
<213> ORGANISM: Artificial Sequence
<220> FEATURE:
<223> OTHER INFORMATION: mutated furin cleavage site

<400> SEQUENCE: 17

```
Gly Arg Arg Gln Gln Arg
1               5
```

<210> SEQ ID NO 18
<211> LENGTH: 6
<212> TYPE: PRT
<213> ORGANISM: Unknown
<220> FEATURE:
<223> OTHER INFORMATION: furin cleavage site

<400> SEQUENCE: 18

```
Lys Lys Arg Lys Arg Arg
1               5
```

<210> SEQ ID NO 19
<211> LENGTH: 539
<212> TYPE: PRT
<213> ORGANISM: Artificial Sequence
<220> FEATURE:
<223> OTHER INFORMATION: modified RSV F protein

<400> SEQUENCE: 19

```
Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Gln Lys Gln Gln Ala
            100                 105                 110

Ile Ala Ser Gly Val Ala Val Ser Lys Val Leu His Leu Glu Gly Glu
        115                 120                 125

Val Asn Lys Ile Lys Ser Ala Leu Leu Ser Thr Asn Lys Ala Val Val
    130                 135                 140
```

```
Ser Leu Ser Asn Gly Val Ser Val Leu Thr Ser Lys Val Leu Asp Leu
145                 150                 155                 160

Lys Asn Tyr Ile Asp Lys Gln Leu Leu Pro Ile Val Asn Lys Gln Ser
            165                 170                 175

Cys Ser Ile Ser Asn Ile Glu Thr Val Ile Glu Phe Gln Gln Lys Asn
        180                 185                 190

Asn Arg Leu Leu Glu Ile Thr Arg Glu Phe Ser Val Asn Ala Gly Val
    195                 200                 205

Thr Thr Pro Val Ser Thr Tyr Met Leu Thr Asn Ser Glu Leu Leu Ser
210                 215                 220

Leu Ile Asn Asp Met Pro Ile Thr Asn Asp Gln Lys Lys Leu Met Ser
225                 230                 235                 240

Asn Asn Val Gln Ile Val Arg Gln Gln Ser Tyr Ser Ile Met Ser Ile
                245                 250                 255

Ile Lys Glu Glu Val Leu Ala Tyr Val Val Gln Leu Pro Leu Tyr Gly
            260                 265                 270

Val Ile Asp Thr Pro Cys Trp Lys Leu His Thr Ser Pro Leu Cys Thr
            275                 280                 285

Thr Asn Thr Lys Glu Gly Ser Asn Ile Cys Leu Thr Arg Thr Asp Arg
290                 295                 300

Gly Trp Tyr Cys Asp Asn Ala Gly Ser Val Ser Phe Phe Pro Gln Ala
305                 310                 315                 320

Glu Thr Cys Lys Val Gln Ser Asn Arg Val Phe Cys Asp Thr Met Asn
                325                 330                 335

Ser Leu Thr Leu Pro Ser Glu Val Asn Leu Cys Asn Val Asp Ile Phe
            340                 345                 350

Asn Pro Lys Tyr Asp Cys Lys Ile Met Thr Ser Lys Thr Asp Val Ser
            355                 360                 365

Ser Ser Val Ile Thr Ser Leu Gly Ala Ile Val Ser Cys Tyr Gly Lys
370                 375                 380

Thr Lys Cys Thr Ala Ser Asn Lys Asn Arg Gly Ile Ile Lys Thr Phe
385                 390                 395                 400

Ser Asn Gly Cys Asp Tyr Val Ser Asn Lys Gly Val Asp Thr Val Ser
                405                 410                 415

Val Gly Asn Thr Leu Tyr Tyr Val Asn Lys Gln Glu Gly Lys Ser Leu
            420                 425                 430

Tyr Val Lys Gly Glu Pro Ile Ile Asn Phe Tyr Asp Pro Leu Val Phe
            435                 440                 445

Pro Ser Asp Glu Phe Asp Ala Ser Ile Ser Gln Val Asn Glu Lys Ile
450                 455                 460

Asn Gln Ser Leu Ala Phe Ile Arg Lys Ser Asp Glu Leu Leu His Asn
465                 470                 475                 480

Val Asn Ala Gly Lys Ser Thr Thr Asn Ile Met Ile Thr Thr Ile Ile
                485                 490                 495

Ile Val Ile Ile Val Ile Leu Leu Ser Leu Ile Ala Val Gly Leu Leu
            500                 505                 510

Leu Tyr Cys Lys Ala Arg Ser Thr Pro Val Thr Leu Ser Lys Asp Gln
            515                 520                 525

Leu Ser Gly Ile Asn Asn Ile Ala Phe Ser Asn
            530                 535

<210> SEQ ID NO 20
<211> LENGTH: 25
<212> TYPE: PRT
```

```
<213> ORGANISM: Respiratory syncytial virus

<400> SEQUENCE: 20

Met Glu Leu Leu Ile Leu Lys Ala Asn Ala Ile Thr Thr Ile Leu Thr
1               5                   10                  15

Ala Val Thr Phe Cys Phe Ala Ser Gly
            20                  25
```

METHODS AND COMPOSITIONS FOR TREATING RESPIRATORY DISEASE

CROSS REFERENCE TO RELATED APPLICATIONS

This application is a national phase filing under 35 U.S.C. § 371 of International Patent Application No. PCT/US2018/043431, filed Jul. 24, 2018, which claims the benefit of priority to U.S. Provisional Application Nos. 62/536,235, filed Jul. 24, 2017, the disclosures of which are incorporated herein for all purposes.

This application incorporates the disclosures of U.S. application Ser. No. 15/257,436 filed Sep. 6, 2016 and U.S. Provisional Application Ser. No. 62/213,947 filed Sep. 3, 2015; 62/255,786 filed Nov. 16, 2015, 62/309,216 filed Mar. 16, 2016, and 62/350,973 filed Jun. 16, 2016 in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_075_01WO_SeqList_ST25.txt, date recorded: Jul. 19, 2018; file size: ~67 kilobytes).

TECHNICAL FIELD

The present disclosure is generally related to nanoparticles, and immunogenic compositions containing them, useful for treating respiratory diseases and preventing exacerbations associated with respiratory diseases. The nanoparticles provide antigens, for example, glycoprotein antigens, associated with a detergent core and are typically produced using recombinant approaches. The nanoparticles reduced chronic obstructive pulmonary (COPD) exacerbations and associated hospitalizations, particularly in elderly populations. The disclosure also provides compositions containing the nanoparticles, methods for producing them, and methods of treating respiratory diseases (e.g. COPD) and preventing further exacerbations.

BACKGROUND

Respiratory and infectious diseases remain a problem throughout the world. While progress has been made on developing vaccines against some pathogens, many remain a threat to human health. Most notoriously HIV, for which a vaccine remains elusive. Attempts have been made to produce vaccines to certain pathogens but have resulted in failure that caused additional pathology.

The World Health Organization estimates 6% of the all deaths worldwide, over 3 million deaths a year, are attributed to chronic obstructive pulmonary disease (COPD), one of the leading respiratory diseases in the world. Exacerbations of COPD have a profound detrimental effect on the patient and impose significant burden on healthcare resources. There is clear evidence of irrevocable decline in pulmonary function after each exacerbation. Prevention and treatment of exacerbations are major objectives of clinical management of COPD (See, Decramer M, et al., (2008) "Targeting the COPD Exacerbation" *J Respir Med* 102:S3-S15 and Rabe K F, et al., (2007) "Global strategy for diagnosis, management, and prevention of chronic obstructive pulmonary disease: GOLD Executive Summary" *Am J Respir Crit Care Med* 176:532-555).

Among other treatment options, the American Lung Association recommends immunizations to COPD patients, particularly yearly influenza and pneumonia vaccinations. Therefore, there is continuing interest in producing therapeutic and prophylactic medicines to reduce or eliminate exacerbations in the COPD population to reduce disease burden, and associated costs.

SUMMARY OF THE INVENTION

The present disclosure provides nanoparticle suitable for treating respiratory diseases and disorders. In particular aspects, the nanoparticle treats chronic obstructive pulmonary disorder (COPD). In other aspects, the nanoparticle prevents exacerbations of COPD in response to respiratory insult; for example, exposure to pathogens.

In some embodiments, the nanoparticles induce immune responses against pathogens. In some embodiments, the pathogen is a virus and, typically, the antigen used to produce a viral nanoparticle is a viral glycoprotein.

In one aspect, the disclosure provides nanoparticles containing viral proteins that have enhanced stability. In some embodiments, the disclosure comprises a vaccine composition comprising a nanoparticle comprising a nonionic detergent, a viral glycoprotein, and a pharmaceutical buffer. In typical embodiments, the nonionic detergent may be selected from the group consisting of PS20, PS40, PS60, PS65, and PS80. In some embodiments, the composition does not comprise any free nonionic detergent. One or more glycoprotein antigen molecules surround a detergent core, which contains the nonionic detergent, and this provides a nanoparticle structure that promotes immunogenicity and inhibits degradation of the antigen.

In some embodiments, antigen is selected from the group consisting of an RSV F protein, an influenza HA protein, an influenza NA protein, and combinations thereof. Typically, the antigen is a glycoprotein.

Optionally, the RSV F protein is a trimeric RSV F protein. The RSV F protein induces the production of neutralizing antibodies. In further embodiments, the neutralizing antibodies recognize the RSV F protein in a post-fusion state and/or a pre-fusion state. In a further aspect, each PS80 particle may comprise between 4 and 7 RSV F proteins.

In some embodiments, an RSV F composition may comprise sodium phosphate at a concentration of between 15 mM and 25 mM; NaCl at a concentration of between 125 mM and 175 mM; histidine between 0.25% and 2% w/v; and the composition pH is between 5.8 and 7.2.

In some embodiments, an HA or NA influenza composition may comprise sodium phosphate at a concentration of between 15 mM and 25 mM; NaCl at a concentration of between 125 mM and 300 mM; histidine between 0.25% and 2% w/v; and the composition pH is above pH 6.8 and typically below about pH 8.0.

In some embodiments, the composition comprises an adjuvant. In further embodiments, the adjuvant is alum or a saponin-based matrix adjuvant. In some embodiments, the composition does not comprise an adjuvant.

In some embodiments, a method of preventing infection comprises administering one or more doses of the vaccine composition. In some embodiments of the method, a single dose of the composition is administered and induces a protective immune response. In some embodiments of the method, each dose consists of between about 100 µg and about 150 µg of the protein antigen. In further embodiments of the method, the one or more doses are administered subcutaneously. In some embodiments of the method, the composition comprises an adjuvant. In a further embodiment of the method, the adjuvant is alum. In some embodiments of the method, the composition is free of adjuvants.

In some embodiments of the method, one or more doses of the composition are administered to an adult. In further embodiments of the method, the adult is over the age of 75, over 70, over 65, over 60, over 55, over 50, or over 45. Thus, in particular aspects, the adult may be about 45 to about 75.

For RSV vaccine, in some embodiments, a composition comprises a heterologous population of at least three RSV F nanoparticle types, wherein each nanoparticle comprises at least one RSV F protein trimer surrounding a detergent-containing core that comprises PS80, and wherein the first RSV F nanoparticle type comprises anisotropic rods, wherein the second RSV F nanoparticle type comprises spherical oligomers, and wherein the third RSV F nanoparticle type comprises intermediates of anisotropic rods and spherical oligomers.

In some embodiments, a method of manufacturing an RSV F protein nanoparticle comprises preparing an RSV F protein extract from a host cell using a first detergent and exchanging the first detergent for a second detergent, wherein the second detergent is PS80, and whereby the nanoparticle exhibits enhanced stability. In a further embodiment of the method, the first detergent is NP-9. In some embodiments of the method, the enhanced stability is selected from protease resistance, oxidative stress resistance, thermal stress resistance, and resistance to agitation. In some embodiments of the method, the molar ratio of PS80:RSV F protein is about 35 to about 65.

In some embodiments, an RSV F nanoparticle comprises one or more RSV F protein trimers associated with a PS80 detergent core. The RSV F nanoparticle, the nanoparticle has an average diameter of about 20 nm to about 60 nm as measured by dynamic light scattering. In some embodiments of the RSV F nanoparticle, each RSV F protein trimer contains an RSV F protein selected from the group consisting of RSV F proteins having a deletion of 1 to 10 amino acids corresponding to residues 137-146 of SEQ ID NO:2. In some embodiments of the RSV F nanoparticle, each RSV F protein trimer contains an RSV F proteins selected from the group consisting of RSV F proteins having a deletion of 1 to 10 amino acids corresponding to residues 137-146 of SEQ ID NO:2 and an inactivated primary fusion cleavage site.

In some embodiments of the RSV F nanoparticle, the RSV F protein comprises a deletion of ten amino acids corresponding to residues 137-146 or SEQ ID NO:2, and inactivation of the primary furin cleavage site by mutation of arginine residues at positions 133, 135, and 136 to glutamine. In further embodiments of the RSV F nanoparticle, the RSV F protein comprises or consists of SEQ ID NO:19, which is the mature peptide. In certain embodiments of the RSV F nanoparticle, the RSV F protein comprises or consists of SEQ ID NO:8. Vaccine formulations containing RSV F nanoparticles comprise substantially of the mature peptide with some full-length peptide (SEQ ID NO:8). Over time, small amount of truncated RSV F peptide may arise due to proteolysis. Advantageously, however, the RSV F nanoparticles disclosed herein minimize such degradation and provide extended stability.

Similarly, nanoparticles containing RSV F proteins combined with influenza proteins, either HA, NA or both, are provided.

BRIEF DESCRIPTION OF THE FIGURES

FIG. 1 depicts the amino acid sequence of a modified RSV F protein (SEQ ID NO:19); with the F1 domain in light-shaded text (residues 1-84), the F2 domain in dark-shaded text (residues 85-539), black lines connecting cysteines that form disulfide bonds, underlined asparagines indicate N-linked glycosylation sites, light-shaded vertical dotted lines indicate a furin cleavage site, and dark-shaded vertical dotted lines indicate a major cleavage site.

FIG. 2 features electron micrographs of RSV F nanoparticles with RSV F protein trimers associated with cores of PS80. Multiple RSV F trimers associate with each particle (40-50 nm diameter).

FIG. 3 depicts the analyses of hospitalizations for all-cause (not associated with RSV detection) COPD exacerbation in the E-301 and E201 studies.

FIG. 4 depicts a graph detailing the decline in populations free of hospitalization due to COPD exacerbation over time in the E-301 study.

DETAILED DESCRIPTION

Disclosed herein are nanoparticles for treating respiratory diseases and disorders, methods for producing and administering them and vaccine compositions containing them. The nanoparticle provides antigen surrounding and associated with a detergent core that result in a structure that provides enhanced stability by numerous measures. Without being bound by theory, the immune response and associated protection induced by a disclosed nanoparticle results in the reduction of exacerbations of a respiratory disease or disorder (e.g. COPD). The detergent core and antigen associate via a physico-chemical interaction mediated by the properties of the antigen and detergent. In addition, the nanoparticles offer especially good antigen presentation to immune systems which, without being bound by theory, is thought to result from the orientation of the antigens around the detergent core.

In one aspect, the disclosure provides compositions containing recombinant viral glycoprotein nanoparticles. In particular aspects, the glycoproteins are recombinantly expressed in a suitable host cell. In one embodiment, the host cell is an insect cell. In an exemplary embodiment, the insect cell is an Sf9 cell.

In particular aspects, the disclosure provides immunogenic compositions comprising one or more viral glycoprotein species in a nanoparticle structure where the glycoprotein is in the form of a trimer and each nanoparticle contains at least one trimer associated with a non-ionic detergent core. In particular aspects, a nanoparticle consists of an antigen, such as a viral glycoprotein, from only one pathogen.

The nanoparticles may be used to treat a respiratory disease or disorder. In some embodiments, the nanoparticles are used to treat COPD. In some embodiments, the nanoparticles reduce incidences of exacerbation of COPD in response to respiratory insult such as a pathogen or other environmental COPD trigger.

The nanoparticles may be used for the prevention and/or treatment of viral infection. Thus, in another aspect, the disclosure provides a method for eliciting an immune response against a virus. The method involves administering an immunologically effective amount of a composition containing a nanoparticle to a subject.

The disclosure provides vaccine compositions comprising the nanoparticle. Compositions may contain nanoparticles having antigens from multiple pathogens. In some aspects, the vaccine composition may contain nanoparticles with antigens from more than one viral strain from the same species of virus. In aspects, the vaccine composition may contain nanoparticles with antigens from different virus species. In another embodiment, the disclosures provide for a pharmaceutical pack or kit comprising one or more containers filled with one or more of the components of the vaccine compositions.

In another embodiment, the disclosure provides a method of formulating a vaccine composition that induces immunity to an infection or at least one disease symptom thereof to a mammal, comprising adding to the composition an effective dose of a nanoparticle. The disclosed nanoparticles are useful for preparing compositions that stimulate an immune response that confers immunity or substantial immunity to infectious agents. Thus, in one embodiment, the disclosure provides a method of inducing immunity to infections or at least one disease symptom thereof in a subject, comprising administering at least one effective dose of a nanoparticle.

In some embodiments, the nanoparticles are administered with an adjuvant. In other aspects, the nanoparticles are administered without an adjuvant. In some aspects, the adjuvant may be bound to the nanoparticle, such as by a non-covalent interaction. In other aspects, the adjuvant is co-administered with the nanoparticle but the adjuvant and nanoparticle do not interact substantially.

Also provided herein are methods of manufacturing the nanoparticles and vaccine compositions. Advantageously, the methods provide nanoparticles that are substantially free from contamination by other proteins, such as proteins associated with recombinant expression of proteins in baculovirus/Sf9 systems.

Definitions

As used herein, and in the appended claims, the singular forms "a", "an", and "the" include plural referents unless the context clearly dictates otherwise. Thus, for example, reference to "a protein" can refer to one protein or to mixtures of such protein.

As used herein, the term "adjuvant" refers to an agent that, when used in combination with an immunogen, augments or otherwise alters or modifies the immune response induced against the immunogen. Modification of the immune response may include intensification or broadening the specificity of either or both antibody and cellular immune responses. Vaccine compositions may include effective amounts of one or more adjuvants.

As used herein, the term "about" or "approximately" when preceding a numerical value indicates the value plus or minus a range of 10%. For example, "about 100" encompasses 90 and 110.

As used herein, the terms "immunogen," "antigen," and "epitope" refer to substances such as proteins, including glycoproteins, and peptides that are capable of eliciting an immune response.

As used herein, an "immunogenic composition" is a composition that comprises an antigen where administration of the composition to a subject results in the development in the subject of a humoral and/or a cellular immune response to the antigen.

As used herein, a "subunit" composition, for example a vaccine, that includes one or more selected antigens but not all antigens from a pathogen. Such a composition is substantially free of intact virus or the lysate of such cells or particles and is typically prepared from at least partially purified, often substantially purified immunogenic polypeptides from the pathogen. The antigens in the subunit composition disclosed herein are typically prepared recombinantly, often using a baculovirus system.

As used herein, "substantially" refers to a substance (e.g. a compound, polynucleotide, or polypeptide) or a process step, such that the substance forms the majority percent of the sample in which it is contained, or a process step is largely complete. For example, in a sample, a substantially purified component comprises 85%, preferably 85%-90%, more preferably at least 95%-99.5%, and most preferably at least 99% of the sample. If a component is substantially replaced the amount remaining in a sample is less than or equal to about 0.5% to about 10%, preferably less than about 0.5% to about 1.0%.

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (1 month to 24 months), or a neonate (up to 1 month). In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. Pharmaceutically acceptable carriers or excipients may be included in the compositions disclosed herein.

As used herein, "respiratory disease" or "respiratory disorder" means diseases or disorder of the airways and/or other structures of the lung. This includes but is not limited to chronic obstructive pulmonary disease (COPD), asthma, allergic rhinitis and sinusitis, bronchiectasis, and pulmonary hypertension. COPD refers to a group of diseases that share symptoms including on ore more of airflow blockage and breathing-related problems including emphysema, chronic bronchitis, and in some cases asthma (See cdc_[.]gov/tobacco/campaign/tips/diseases/copd.html)

As used herein, the term "about" means plus or minus 10% of the indicated numerical value.

Overview

COPD symptoms typically appear when the subject already has significant lung damage, and the symptoms often worsen over time. COPD is a common outcome for subjects exhibiting suffering from emphysema or chronic bronchitis. In chronic bronchitis, the main symptom is a daily cough and mucus (sputum) production at least three months a year for two consecutive years. Emphysema is a condition in which the alveoli at the end of the smallest air passages (bronchioles) of the lungs are destroyed, typically from smoking. Other symptoms of COPD may include: shortness of breath, especially during physical activities, wheezing, chest tightness, a chronic cough, often with mucus, and blueness of the lips or fingernail beds (cyanosis).

Subjects with COPD are also likely to experience episodes called exacerbations, during which these symptoms become worse than usual day-to-day variation and persist for at least several days. The exacerbations typically occur in response to an environmental insult encountered by the subject. A variety of biological and non-biological environmental insults may cause exacerbations in COPD patients including second hand cigarette smoke, fumes from gasoline, bacteria, and viral infections.

The methods and compositions used herein may be used to reduce or eliminate exacerbations or the severity of one or more of the symptoms associated with the exacerbations. The immunogenic compositions of the disclosure contain one or more antigens derived from pathogens in a nanoparticle format.

Antigens derived from pathogens are combined with non-ionic detergents to provide nanoparticles surrounding a detergent core that have improved stability and excellent immunogenicity and treat respiratory diseases and disorders. The disclosure also provides for methods and compositions for vaccinating a subject against pathogens to treat respiratory diseases and disorders. The antigen is typically a viral protein, often a glycoprotein. Also disclosed are compositions containing the nanoparticles which find use as vaccine compositions to treat respiratory diseases and disorders.

In particular aspects, the compositions contains nanoparticles that induce immune responses against RSV alone. In other aspects the composition contains nanoparticles that contain glycoproteins from against RSV; for example an RSV-F protein, and one or more influenza HA glycoproteins strains (e.g. nanoparticles comprising HA glycoproteins from 1, 2, 3 or 4 different influenza strains).

In additional to the nanoparticles, the subject may also be administered additional immunogenic compositions. For example, the subject may be administered compositions to induce an immune response against one or more of *Streptococcus pneumoniae, Bordetella pertussis* (whooping cough agent), *Haemophilus influenzae* type b (Hib), and measles.

It is a notable result of the immunogenic compositions disclosed herein that administering nanoparticle compositions containing an RSV F glycoprotein reduces hospitalization for "all-cause" COPD exacerbations, meaning that the response to the composition did not only reduce RSV-stimulated exacerbations but also had a more general benefit, reducing all causes of exacerbations. See FIG. 4 and FIG. 5. Thus, compositions containing the nanoparticles are useful for administering to subjects having COPD to prevent exacerbations in responses to environmental insults.

Nanoparticle Structure and Morphology

Nanoparticles of the present disclosure comprise glycoprotein antigens associated with a non-ionic detergent core. FIG. 2 illustrates an example of multiple RSV F antigens associated with the detergent core.

In particular embodiments, the nanoparticles are composed of multiple protein trimers surrounding a non-ionic detergent core. For example, each nanoparticle may contain 1, 2, 3, 4, 5, 6, 7, 8, 9, 10, 11, 12, or 15 trimers. Typically, each nanoparticle contains 2 to 9 trimers. In particular embodiments, each nanoparticle contains 2 to 6 trimers. Compositions disclosed herein may contain nanoparticles having different numbers of trimers. For example, a composition may contain nanoparticles where the number of trimers ranges from 2-9; in other embodiments, the nanoparticles in a composition may contain from 2-6 trimers. In particular embodiments, the compositions contain a heterogeneous population of nanoparticles having 2 to 6 trimers per nanoparticle, or 2 to 9 trimers per nanoparticle. In other embodiments, the compositions may contain a substantially homogenous population of nanoparticles. For example, the population may contain about 95% nanoparticles having 5 trimers.

The antigens are associated with the non-ionic detergent-containing core of the nanoparticle. Typically, the detergent is selected from polysorbate-20 (PS20), polysorbate-40 (PS40), polysorbate-60 (PS60), polysorbate-65 (PS65) and polysorbate-80 (PS80). The presence of the detergent facilitates formation of the nanoparticles by forming a core that organizes and presents the antigens. Thus, in certain embodiments, the nanoparticles may contain the antigens assembled into multi-oligomeric glycoprotein-PS80 protein-detergent nanoparticles with the head regions projecting outward and hydrophobic regions and PS80 detergent forming a central core surrounded by the antigens.

The nanoparticles disclosed herein range in Z-ave size from about 20 nm to about 60 nm, about 20 nm to about 50 nm, about 20 nm to about 45 nm, or about 25 nm to about 45 nm. Particle size (Z-ave) is measured by dynamic light scattering (DLS) using a Malvern Zetasizer, unless otherwise specified.

Several nanoparticle types may be included in vaccine compositions disclosed herein. In some aspects, the nanoparticle type is in the form of an anisotropic rod, which may be a dimer or a monomer. In other aspects, the nanoparticle type is a spherical oligomer. In yet other aspects, the nanoparticle may be described as an intermediate nanoparticle, having sedimentation properties intermediate between the first two types. Formation of nanoparticle types may be regulated by controlling detergent and protein concentration during the production process.

Nanoparticle type may be determined by measuring sedimentation co-efficient.

Nanoparticle Production

The nanoparticles of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The antigens contained in the nanoparticles are typically produced by recombinant expression in host cells. Standard recombinant techniques may be used. Typically, the proteins are expressed in insect host cells using a baculovirus system. In preferred embodiments, the baculovirus is a cathepsin-L knock-out baculovirus. In other preferred embodiments, the bacuolovirus is a chitinase knock-out baculovirus. In yet other preferred embodiments, the baculovirus is a double knock-out for both cathepsin-L and chitinase. High level expression may be obtained in insect cell expression systems. Non limiting examples of insect cells are, *Spodoptera frugiperda* (Sf) cells, e.g. Sf9, Sf21, *Trichoplusia ni* cells, e.g. High Five cells (also called BTI-TN-5B1-4), and *Drosophila* S2 cells.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Detergent Extraction and Purification of Nanoparticles

After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and tergitol, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. In certain embodiments, the range may be about 0.1% to about 0.3%. Preferably, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), Brij® 35, Brij®56, Brij® 72, Brij® 76, Brij® 92V, Brij® 97, Brij® 58P, Cremophor® EL, Decaethyleneglycol monododecyl ether, N-Decanoyl-N-methylglucamine, n-Decyl alpha-Dglucopyranoside, Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-0-(N-heptylcarbamoyl)-alpha-D-glucopyranoside, Nonaethylene glycol monododecyl ether, N-Nonanoyl-N-methylglucamine, N-NonanoylN-methylglucamine, Octaethylene glycol monodecyl ether, Octaethylene glycolmonododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from Quillaja bark, Span® 20, Span® 40, Span® 60, Span® 65, Span® 80, Span® 85, Tergitol Type 15-S-12, Tergitol Type 15-S-30, Tergitol Type 15-S-5, Tergitol Type 15-S-7, Tergitol Type 15-S-9, Tergitol Type NP-10, Tergitol Type NP-4, Tergitol Type NP-40, Tergitol, Type NP-7 Tergitol Type NP-9, Tergitol Type TMN-10, Tergitol Type TMN-6, Triton X-100 or combinations thereof.

The nanoparticles may then be isolated from cellular debris using centrifugation. In some embodiments, gradient centrifugation, such as using cesium chloride, sucrose and iodixanol, may be used. Other techniques may be used as alternatives or in addition, such as standard purification techniques including, e.g., ion exchange, affinity, and gel filtration chromatography.

For example, the first column may be an ion exchange chromatography resin, such as Fractogel® EMD TMAE (EMD Millipore), the second column may be a lentil (*Lens culinaris*) lectin affinity resin, and the third column may be a cation exchange column such as a Fractogel® EMD S03 (EMD Millipore) resin. In other aspects, the cation exchange column may be an MMC column or a Nuvia C Prime column (Bio-Rad Laboratories, Inc). Preferably, the methods disclosed herein do not use a detergent extraction column; for example a hydrophobic interaction column. Such a column is often used to remove detergents during purification but may negatively impact the methods disclosed here.

Detergent Exchange

To form nanoparticles, the first detergent, used to extract the protein from the host cell is substantially replaced with a second detergent to arrive at the nanoparticle structure. NP-9 is a preferred extraction detergent. Typically, the nanoparticles do not contain detectable NP-9 when measured by HPLC. The second detergent is typically selected from the group consisting of PS20, PS40, PS60, PS65, and PS80. Preferably, the second detergent is PS80. To maintain the stability of the nanoparticle formulations, the ratio of the second detergent and protein is maintained within a certain range.

In particular aspects, detergent exchange is performed using affinity chromatography to bind glycoproteins via their carbohydrate moiety. For example, the affinity chromatography may use a legume lectin column. Legume lectins are proteins originally identified in plants and found to interact specifically and reversibly with carbohydrate residues. See, for example, Sharon and Lis, "Legume lectins—a large family of homologous proteins," FASEB J. 1990 November; 4(14):3198-208; Liener, "The Lectins: Properties, Functions, and Applications in Biology and Medicine," Elsevier, 2012. Suitable lectins include concanavalin A (con A), pea lectin, sainfoin lect, and lentil lectin. Lentil lectin is a preferred column for detergent exchange due to its binding properties. See, for instance, Example 10. Lectin columns are commercially available; for example, Capto Lentil Lectin, is available from GE Healthcare. In certain aspects, the lentil lectin column may use a recombinant lectin. At the molecular level, it is thought that the carbohydrate moieties bind to the lentil lectin, freeing the amino acids of the protein to coalesce around the detergent resulting in the formation of a detergent core providing nanoparticles having multiple copies of the antigen, e.g., glycoprotein oligomers which can be dimers, trimers, or tetramers anchored in the detergent.

The detergent, when incubated with the protein to form the nanoparticles during detergent exchange, may be present at up to about 0.1% (w/v) during early purifications steps and this amount is lowered to achieve the final nanoparticles having optimum stability. For example, the non-ionic detergent (e.g., PS80) may be about 0.03% to about 0.1%. Preferably, for improved stability, the nanoparticle contains about 0.03% to about 0.05% PS80. Amounts below about 0.03% PS80 in formulations do not show as good stability. Further, if the PS80 is present above about 0.05%, aggregates are formed. Accordingly, about 0.03% to about 0.05% PS80 provides structural and stability benefits that allow for long-term stability of nanoparticles with reduced degradation.

Detergent exchange may be performed with proteins purified as discussed above and purified, frozen for storage, and then thawed for detergent exchange.

Enhanced Stability and Enhanced Immunogenicity of Nanoparticles

Without being bound by theory, it is thought that associating the antigen with a non-ionic detergent core offers superior stability and antigen presentation. The nanoparticles disclosed herein provide surprisingly good stability and immunogenicity.

It is thought that the position of the glycoprotein anchored into the detergent core provides enhanced stability by reducing undesirable interactions. For example, the improved protection against protease-based degradation may be achieved through a shielding effect whereby anchoring the glycoproteins into the core at the molar ratios disclosed herein results in steric hindrance blocking protease access.

Nanoparticle Antigens

In typical embodiments, the antigens used to produce the nanoparticles are viral proteins. In some aspects, the proteins may be modified but retain the ability to stimulate immune responses against the natural peptide. In some aspects, the protein inherently contains or is adapted to contain a transmembrane domain to promote association of the protein into a detergent core. Often the protein is naturally a glycoprotein.

RSV Antigens

In one aspect, the virus is Respiratory Syncytial Virus (RSV) and the viral antigen is the Fusion (F) glycoprotein. The structure and function of RSV F proteins is well characterized. Suitable RSV-F proteins for use in the compositions described herein can be derived from RSV strains such as A2, Long, ATCC VR-26, 19, 6265, E49, E65, B65, RSB89-6256, RSB89-5857, RSB89-6190, and RSB89-6614. In certain embodiments, RSV F proteins are mutated compared to their natural variants. These mutations confer desirable characteristics, such as improved protein expression, enhanced immunogenicity and the like. Additional information describing RSV-F protein structure can be found at Swanson et al. A Monomeric Uncleaved Respiratory Syncytial Virus F Antigen Retains Prefusion-Specific Neutralizing Epitopes. Journal of Virology, 2014, 88, 11802-11810. Jason S. McLellan et al. Structure of RSV Fusion Glycoprotein Trimer Bound to a Prefusion-Specific Neutralizing Antibody. Science, 2013, 340, 1113-1117.

The primary fusion cleavage is located at residues 131 to 136 corresponding to SEQ ID NO:2. Inactivation of the primary fusion cleavage site may be achieved by mutating residues in the site, with the result that furin can no longer recognize the consensus site. For example, inactivation of the primary furin cleavage site may be accomplished by introducing at least one amino acid substitution at positions corresponding to arginine 133, arginine 135, and arginine 136 of the wild-type RSV F protein (SEQ ID NO:2). In particular aspects, one, two, or all three of the arginines are mutated to glutamine. In other aspects, inactivation is accomplished by mutating the wild-type site to one of the following sequences: KKQKQQ (SEQ ID NO: 14), QKQKQQ (SEQ ID NO:15), KKQKRQ (SEQ ID NO: 16), and GRRQQR (SEQ ID NO: 17).

In particular aspects, from 1 to 10 amino acids of the corresponding to acids 137 to 145 of SEQ ID NO: 2 may be deleted, including the particular examples of suitable RSV F proteins shown below. Each of SEQ ID NOS 3-13 may optionally be prepared with an active primary fusion cleavage site KKRKRR (SEQ ID NO:18). The wild type strain in SEQ ID NO: 2 has sequencing errors (A to P, V to I, and V to M) that are corrected in SEQ ID NOS:3-13. Following expression of the RSV-F protein in a host cell, the N-terminal signal peptide is cleaved to provide the final sequences. Typically, the signal peptide is cleaved by host cell proteases. In other aspects, however, the full-length protein may be isolated from the host cell and the signal peptide cleaved subsequently. The N-terminal RSV F signal peptide consists of amino acids of SEQ ID NO: 20 (MELLILKANAITTILTAVTFCFASG). Thus, for example, following cleavage of the signal peptide from SEQ ID NO:8 during expression and purification, a mature protein having the sequence of SEQ ID NO: 19 is obtained and used to produce a RSV F nanoparticle vaccine. See FIG. 1. Optionally, one or more up to all of the RSV F signal peptide amino acids may be deleted, mutated, or the entire signal peptide may be deleted and replaced with a different signal peptide to enhance expression. An initiating methionine residue is maintained to initiate expression.

| Expressed Protein SEQ ID NO | Fusion Domain Deletion | Primary Fusion Cleavage Site sequence |
| --- | --- | --- |
| 1 | Wild type Strain A2 (nucleic) | KKRKRR (active) |
| 2 | Wild type Strain A2 (protein) | KKRKRR (active) |
| 3 | Deletion of 137 (Δ1) | KKQKQQ (inactive) |

-continued

| Expressed Protein SEQ ID NO | Fusion Domain Deletion | Primary Fusion Cleavage Site sequence |
|---|---|---|
| 4 | Deletion of 137-138 (Δ2) | KKQKQQ (inactive) |
| 5 | Deletion of 137-139 (Δ3) | KKQKQQ (inactive) |
| 6 | Deletion of 137-140 (Δ4) | KKQKQQ (inactive) |
| 7 | Deletion of 137-141 (Δ5) | KKQKQQ (inactive) |
| 8 | Deletion of 137-146 (Δ10) | KKQKQQ (inactive) |
| 9 | Deletion of 137-142 (Δ6) | KKQKQQ (inactive) |
| 10 | Deletion of 137-143 (Δ7) | KKQKQQ (inactive) |
| 11 | Deletion of 137-144 (Δ8) | KKQKQQ (inactive) |
| 12 | Deletion of 137-145 (Δ9) | KKQKQQ (inactive) |
| 13 | Deletion of 137-145 (Δ9) | KKRKRR (active) |

In some aspects, the RSV F protein disclosed herein is only altered from a wild-type strain by deletions in the fusion domain, optionally with inactivation of the primary cleavage site. In other aspects, additional alterations to the RSV F protein may be made. Typically, the cysteine residues are mutated. Typically, the N-linked glycosylation sites are not mutated. See FIG. 1. Additionally, the antigenic site II, also referred to herein as the Palivizumab site because of the ability of the palivizumab antibody to bind to that site, is preserved. The Motavizumab antibody also binds at site 11. Additional suitable RSV-F proteins, incorporated by reference, are found in U.S Publication US 2011/0305727, including in particular, RSV-F proteins containing the sequences spanning residues 100 to 150 as disclosed in FIG. 1C therein.

In certain other aspects, the RSV F1 or F2 domains may have modifications relative to the wild-type strain as shown in SEQ ID NO:2. For example, the F1 domain may have 1, 2, 3, 4, 5, 6, 7, 8, 9, or 10 alterations, which may be mutations or deletions. Similarly, the F2 domain may have 1, 2, 3, 4, 5, 6, 7, 8, 9, or 10 alterations, which may be mutations or deletions. The F1 and F2 domains may each independently retain at least 90%, at least 94% at least 95% at least 96% at least 98% at least 99%, or 100% identity to the wild-type sequence.

In a particular example, an RSV nanoparticle drug product may contain about 0.025% to about 0.03% PS80 with RSV F at a range of about 270 μg/mL to about 300 μg/mL, or about 60 μg/mL to about 300 μg/mL. In other aspects, the nanoparticle drug product may contain about 0.035% to about 0.04% PS80 in a composition with RSV F at 300 μg/mL to about 500 μg/mL. In yet other aspects, the nanoparticle drug product may contain about 0.035% to about 0.04% PS80 in a composition with RSV F at 350-500 μg/mL.

Because the concentrations of antigen and detergent can vary, the amounts of each may be referred as a molar ratio of non-ionic detergent:protein. For example, the molar ratio of PS80 to protein is calculated by using the PS80 concentration and protein concentration of the antigen measured by ELISA/A280 and their respective molecular weights. The molecular weight of PS80 used for the calculation is 1310 and, using RSV F as an example, the molecular weight for RSV F is 65 kD. Molar ratio is calculated as a follows: (PS80 concentration×10×65000)÷(1310×RSV F concentration in mg/mL). Thus, for example, the nanoparticle concentration, measured by protein, is 270 μg/mL and the PS80 concentrations are 0.015% and 0.03%. These have a molar ratio of PS80 to RSV F protein of 27:1 (that is, 0.015×10× 65000/(1310×0.27)) and 55:1, respectively.

In particular aspects, the molar ratio is in a range of about 30:1 to about 80:1, about 30:1 to about 70:1, about 30:1 to about 60:1, about 40:1 to about 70:1, or about 40:1 to about 50:1. Often, the replacement non-ionic detergent is PS80 and the molar ratio is about 30:1 to about 50:1, PS80:protein. For RSV-F glycoprotein, nanoparticles having a molar ratio in a range of 35:1 to about 65:1, and particularly a ratio of about 45:1, are especially stable.

Modified Antigens

The antigens disclosed herein encompass variations and mutants of those antigens. In certain aspects, the antigen may share identity to a disclosed antigen. Generally, and unless specifically defined in context of a specifically identified antigens, the percentage identity may be at least 80%, at least 90%, at least 95%, at least 97%, or at least 98%. Percentage identity can be calculated using the alignment program ClustalW2, available at ebi_[.]ac.uk/Tools/msa/clustalw2/. The following default parameters may be used for Pairwise alignment: Protein Weight Matrix=Gonnet; Gap Open=10; Gap Extension=0.1.

In particular aspects, the protein contained in the nanoparticles consists of that protein. In other aspects, the protein contained in the nanoparticles comprise that protein. Additions to the protein itself may be for various purposes. In some aspects, the antigen may be extended at the N-terminus, the C-terminus, or both. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included.

In some aspects, the antigen may be truncated. For example, the N-terminus may be truncated by about 10 amino acids, about 30 amino acids, about 50 amino acids, about 75 amino acids, about 100 amino acids, or about 200 amino acids. The C-terminus may be truncated instead of or in addition to the N-terminus. For example, the C-terminus may be truncated by about 10 amino acids, about 30 amino acids, about 50 amino acids, about 75 amino acids, about 100 amino acids, or about 200 amino acids. For purposes of calculating identity to the protein having truncations, identity is measured over the remaining portion of the protein.

Combination Nanoparticles

A combination nanoparticle, as used herein, refers to a nanoparticle that induces immune responses against two or more different pathogens. Depending on the particular combination, the pathogens may be different strains or sub-types of the same species or the pathogens may be different species. To prepare a combination nanoparticle, glycoproteins from multiple pathogens may be combined into a single nanoparticle by binding them at the detergent exchange stage. The binding of the glycoproteins to the column followed by detergent exchange permits multiple glycoproteins types to form around a detergent core, to provide a combination nanoparticle.

The disclosure also provides for vaccine compositions that induce immune responses against two or more different pathogens by combining two or more nanoparticles that each induce a response against a different pathogen. Optionally, vaccine compositions may contain one or more combination nanoparticles alone or in combination with additional nanoparticles with the purpose being to maximize the immune response against multiple pathogens while reducing the number of vaccine compositions administered to the subject.

Such compositions are particularly desirable when the pathogens are connected in some aspect. In one example, a composition may contain nanoparticles against the strains identified annually by authorities as forming a particular year's seasonal influenza. Typically, for a seasonal influenza vaccine, a vaccine composition contains RSV antigens combined with HA and/or NA nanoparticles that induce immune responses against a strain of three, four, or five influenza sub-types. Thus, different strains of influenza may be combined in a vaccine composition. In some aspects, the combination nanoparticle may contain an HA protein from a first strain and an NA protein from a second strain. In other aspects, a nanoparticle may contain one or more HA and one or more NA proteins from the same or different sub-types. For example, a nanoparticle may contain one or more HA nanoparticles selected from the sub-types H1, H2, H3, H4, H5, H6, H7, H8, H9, H10, H11, H12, H13, H14, H15 and H16 and/or one or more NA nanoparticles selected from the sub-types N1, N2, N3, N4, N5, N6, N7, N8 and N9. Phylogenetically, the HA and NA proteins are split into groups. For HA, Group 1 contains H1, H2, H5, H6, H8, H9, H11, H12, H13, and H16, and group 2 contains H3, H4, H7, H10, H14, and H15. NA proteins also form two groups: Group 1 contains N1, N4, N5, and N8, and Group 2 contains N2, N3, N6, N7, and N9. In certain aspects, the antigen may have at least 90% identity, at least 95% identity, at least 97% identity, or at least 99% to the native influenza HA protein and/or to the NA protein.

In another example, as discussed above, influenza and RSV both cause respiratory disease exacerbation and HA, NA, and/or RSV F may therefore be mixed into a combination nanoparticle, or multiple nanoparticles may be combined in an immunogenic composition, to induce responses against RSV and one or more influenza strains.

Vaccine Compositions

Compositions disclosed herein may be used either prophylactically or therapeutically, but will typically be prophylactic. Accordingly, the disclosure includes methods for treating or preventing infection. The methods involve administering to the subject a therapeutic or prophylactic amount of the immunogenic compositions of the disclosure. Preferably, the pharmaceutical composition is a vaccine composition that provides a protective effect. In other aspects, the protective effect may include amelioration of a symptom associated with infection in a percentage of the exposed population. For example, depending on the pathogen, the composition may prevent or reduce one or more virus disease symptoms selected from: fever fatigue, muscle pain, headache, sore throat, vomiting, diarrhea, rash, symptoms of impaired kidney and liver function, internal bleeding and external bleeding, compared to an untreated subject.

The nanoparticles may be formulated for administration as vaccines in the presence of various excipients, buffers, and the like. For example, the vaccine compositions may contain sodium phosphate, sodium chloride, and/or histidine. Sodium phosphate may be present at about 10 mM to about 50 mM, about 15 mM to about 25 mM, or about 25 mM; in particular cases, about 22 mM sodium phosphate is present. Histidine may be present about 0.1% (w/v), about 0.5% (w/v), about 0.7% (w/v), about 1% (w/v), about 1.5% (w/v), about 2% (w/v), or about 2.5% (w/v). Sodium chloride, when present, may be about 150 mM. In certain compositions, for example influenza vaccines, the sodium chloride may be present at higher amounts, including about 200 mM, about 300 mM, or about 350 mM.

Certain nanoparticles, particularly RSV F nanoparticles, have improved stability at slightly acidic pH levels. For example, the pH range for composition containing the nanoparticles may be about pH 5.8 to about pH 7.0, about pH 5.9 to about pH 6.8, about pH 6.0 to about pH 6.5, about pH 6.1 to about pH 6.4, about pH 6.1 to about pH 6.3, or about pH 6.2. Typically, the composition for RSV F protein nanoparticles is about pH 6.2. In other nanoparticles, the composition may tend towards neutral; for example, influenza nanoparticles may be about pH 7.0 to pH 7.4; often about pH 7.2.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions. Advantageously, adjuvant-free compositions disclosed herein may provide protective immune responses when administered as a single dose. Alum-free compositions that induce robust immune responses are especially useful in adults about 60 and older.

Aluminum-Based Adjuvants

In some embodiments, the adjuvant may be alum (e.g. $AlPO_4$ or $Al(OH)_3$). Typically, the nanoparticle is substantially bound to the alum. For example, the nanoparticle may be at least 80% bound, at least 85% bound, at least 90% bound or at least 95% bound to the alum. Often, the nanoparticle is 92% to 97% bound to the alum in a composition. The amount of alum is present per dose is typically in a range between about 400 μg to about 1250 μg. For example, the alum may be present in a per dose amount of about 300 μg to about 900 μg, about 400 μg to about 800 μg, about 500 μg to about 700 μg, about 400 μg to about 600 μg, or about 400 μg to about 500 μg. Typically, the alum is present at about 400 μg for a dose of 120 μg of the protein nanoparticle.

Matrix Adjuvants

The Matrix particles of the disclosure are formed using formed using only one saponin fraction. Several approaches for producing saponin fractions to form matrix particles are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semipreparative HPLC with elution using a gradient of from 25% to 60% acetonitrile in acidic water. The fraction referred to herein as "Fraction A" or "QH-A" is the fraction eluted at about 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other usable saponin fractions have been described. Fractions B3, B4 and B4b are described in EP 0436620. Fractions QA1-QA22 are described EP03632279 B2, Q-VAC (Nor-Feed, AS Denmark), *Quillaja saponaria* Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9. In embodiments, the saponin fraction from *Quillaja saponaria* Molina is selected from any one of QA 1-21.

Other saponin fractions, such as QS-7 and QS-21 fractions, their production and their use is described in U.S. Pat. Nos. 5,057,540; 6,231,859; 6,352,697; 6,524,584; 6,846,489; 7,776,343, and 8,173,141. These fractions may be used to produce matrix for use in the methods and compositions disclosed herein.

In some aspects, the compositions containing Matrix particles having only one saponin fraction. In other aspects, the compositions may contain multiple types of Matrix particles, which each contain one saponin fraction per particle type, but the particles have different fractions.

The Matrix particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of matrix particle containing a first saponin fraction with the remaining portion made up by a matrix particle containing a different saponin fraction.

The amounts of each Matrix in the composition may vary as a percentage of the total composition. For example, the amount of Fraction A Matrix may be about 80% (w/w), about 85% (w/w), about 90% (w/w), about 92% (w/w), or about 95% (w/w) in each case with the remainder Fraction C Matrix. Typically a range of about 80% (w/w) to about 95% (w/w) of Fraction A Matrix with the remainder of the composition being Fraction C Matrix. Commonly, about 85% (w/w) Fraction A Matrix with the remainder Fraction C Matrix (i.e., 85:15) is used. A particular example of 85:15 Fraction A Matrix and Fraction C Matrix combination is Matrix-M™ (Novavax AB, Uppsala, Sweden), a mixture of Fraction A Matrix and Fraction C Matrix at a ratio of about 85 to about 15.

Other Adjuvants

In some, compositions other adjuvants may be used in addition or as an alternative. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Other adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/Tween® 80 emulsion. In some embodiments, the adjuvant may be a paucilamellar lipid vesicle; for example, Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant (see, U.S. Pat. Nos. 5,629,021, 6,387,373, and 4,911,928.

Administration and Dosage

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intraarterial, intramuscular, or intrasternal injection, intravenous, or kidney dialytic infusion techniques. Typically, the systemic, parenteral administration is intramuscular injection. As used herein, the term "mucosal administration" includes oral, intranasal, intravaginal, intra-rectal, intra-tracheal, intestinal and ophthalmic administration. Preferably, administration is intramuscular.

Compositions may be administered on a single dose schedule or a multiple dose schedule. Multiple doses may be used in a primary immunization schedule or in a booster immunization schedule. In a multiple dose schedule the various doses may be given by the same or different routes e.g., a parenteral prime and mucosal boost, a mucosal prime and parenteral boost, etc. In some aspects, a follow-on booster dose is administered about 2 weeks, about 3 weeks, about 4 weeks, about 5 weeks, or about 6 weeks after the prior dose. Typically, however, the compositions disclosed herein are administered only once yet still provide a protective immune response.

In some embodiments, the dose, as measured in µg, may be the total weight of the dose including the solute, or the weight of the RSV F nanoparticles, or the weight of the RSV F protein. Dose is measured using protein concentration assay either A280 or ELISA.

The dose of antigen, including for pediatric administration, may be in the range of about 30 µg to about 300 µg, about 90 µg to about 270 µg, about 100 µg to about 160 µg, about 110 µg to about 150 µg, about 120 µg to about 140 µg, or about 140 µg to about 160 µg. In particular embodiments, the dose is about 120 µg, administered with alum. Certain populations may be administered with or without adjuvants. For example, when administered to seniors, preferably there is no alum. In certain aspects, compositions may be free of added adjuvant. In such circumstances, the dose may be increased by about 10% or about 20%.

In some embodiments, the dose may be administered in a volume of about 0.1 mL to about 1.5 mL, about 0.3 mL to about 1.0 mL, about 0.4 mL to about 0.6 mL, or about 0.5 mL, which is a typical amount.

In particular embodiments for an RSV vaccine, the dose may comprise an RSV F protein concentration of about 175 µg/mL to about 325 µg/mL, about 200 µg/mL to about 300 µg/mL, about 220 µg/mL to about 280 µg/mL, or about 240 µg/mL to about 260 µg/mL.

INCORPORATION BY REFERENCE

All references, articles, publications, patents, patent publications, and patent applications cited herein are incorporated by reference in their entireties for all purposes.

EXAMPLES

Example 1

Expression and Purification of an RSV F Protein

An RSV F protein having SEQ ID NO: 8 was expressed in a baculovirus expression system and recombinant plaques expressing the RSV F protein were picked and confirmed. The recombinant virus was then amplified by infection of Sf9 insect cells. A culture of insect cells was infected at ~3 MOI (Multiplicity of infection=virus ffu or pfu/cell) with baculovirus. The culture and supernatant were harvested 48-72 hrs post-infection. The crude cell harvest, approximately 30 mL, was clarified by centrifugation for 15 minutes at approximately 800×g. The resulting crude cell harvests containing the RSV F protein were purified as described below.

Non-ionic surfactant Tergitol® NP-9 (Nonylphenol Ethoxylate) was used in the membrane protein extraction protocol. NP-9 was Crude extraction was further purified by passing through anion exchange chromatography, lentil lectin affinity/HIC and cation exchange chromatography. The washed cells were lysed by detergent treatment and then subjected to low pH treatment which leads to precipitation of BV and Sf9 host cell DNA and protein. The neutralized low pH treatment lysate is clarified and further purified on anion exchange and affinity chromatography before a second low pH treatment is performed.

Affinity chromatography was used to remove Sf9/BV proteins, DNA and NP-9, as well as concentrate the RSV F protein. Briefly, lentil lectin is a metalloprotein containing calcium and manganese, which reversibly binds polysaccharides and glycosylated proteins containing glucose or mannose. The RSV F-containing anion exchange flow through fraction was loaded onto the lentil lectin affinity chromatography resin (Capto Lentil Lectin, GE Healthcare). The glycosylated RSV F protein selectively binds to the resin while non-glycosylated proteins and DNA are removed in the column flow through. Weakly bound glycoproteins were removed by buffers containing high salt and low molar concentration of methyl alpha-D-mannopyranoside (MMP).

In addition, the column washes were also used to detergent exchange the NP-9 detergent with the surfactant polysorbate 80 (PS80). To perform the detergent exchange, the column was incubated with 0.1% PS80 after binding of the RSV F glycoprotein to the lentil lectin column. The RSV F protein was eluted from the lentil lectin column with a high concentration of MMP. After elution, the RSV F protein trimers are assembled into micelle nanoparticles composed of RSV F protein trimers and PS80 contained in a detergent core. After detergent exchange there was a low pH inactivation step followed by incubation on a sulfate column in the presence of buffer with PS80 at 0.1%.

The eluted material was diluted in a solution containing PS80 adequate to provide a Drug Substance (DS) for bulk storage with a molar ratio of PS80:RSV F protein of about 50. The adequate composition of the DS was achieved by combining the RSV F nanoparticles in a solution comprising phosphate buffer at 22 mM sodium phosphate, 0.03% PS80, and a pH of 6.2. At each step during and after detergent exchange, the antigen to PS80 ratio in the composition was maintained at a molar ratio between 35 and 60. The molar ratio was calculated using the PS80 concentration and RSV F concentration, as measured by ELISA/A280, and their respective molecular weights. The molecular weight of PS80 is 1310 and for RSV is 65 kD.

Example 2

Preparation of a Vaccine Composition

To provide nanoparticles for an administered vaccine product, the Drug Substance was diluted into a Drug Product, with a PS80:RSV protein molar ratio of about 50. Drug Substance was thawed, diluted and filled into glass vials or pre-filled syringes for storage at 2-8° C. prior to administration. The nanoparticles bound to alum adjuvant. The alum adjuvant was added and mixed to ensure about 95% of the nanoparticles are bound to the alum is bound, meaning about 0.4 mg per 120 μg dose of RSV F nanoparticle in a 0.5 mL volume.

Example 3

RSV F in Nanoparticles Reduce COPD Exacerbation Hospitalization

In a randomized, placebo-controlled study of 11,856 subjects, aged 60 years or older, a vaccine comprising 135 μg RSV F nanoparticles in the absence of alum reduced all-cause COPD exacerbation hospitalizations (called "E-301" in FIG. 3 and FIG. 4). The subjects were followed for a year to ascertain the safety, immunogenicity, and efficacy of the vaccine. Surprisingly, administration of the RSV F nanoparticle vaccine reduced hospitalization due to COPD exacerbation in both the general populous of the study (p=0.017) and in a subpopulation of the study of subjects previously identified as having baseline COPD (p=0.14).

In a smaller scale, comparable study consisting of 1,600 subjects, aged 60 years or older, the group administered the RSV F nanoparticle vaccine experienced no COPD exacerbation hospitalizations (called "E-201" FIG. 3). The data show that in the E-201 study, 0 of 798 subjects given the vaccine had a hospitalization event compared with 4 of 801 subjects given the placebo, resulting in a 100% vaccine efficacy percentage (VE %).

The invention claimed is:

1. A method of reducing exacerbations of chronic obstructive pulmonary disease (COPD) in a human subject comprising administering a nanoparticle vaccine to the subject, wherein the nanoparticle comprises: a non-ionic detergent core and a viral glycoprotein, wherein the viral glycoprotein is associated with the core and the detergent is present at about 0.03% to about 0.05%, wherein the viral glycoprotein is an RSV F protein.

2. The method of claim 1, wherein the exacerbation is caused by an environmental insult.

3. The method of claim 2, wherein the environmental insult is a pathogen.

4. The method of claim 3, wherein the pathogen is a viral pathogen.

5. The method of claim 4, wherein the viral pathogen is selected from the group consisting of an RSV virus and an influenza virus.

6. The method of claim 1, wherein the incidence of exacerbations is reduced by about 50% as determined by hospitalization rate.

7. The method of claim 6, wherein the human is at least 60 years old.

8. The method of claim 1, wherein the non-ionic detergent is selected from the group consisting of PS20, PS40, PS60, PS65, and PS80.

9. The method of claim 8, wherein the RSV F protein is combined with at least one of an influenza HA protein, and an influenza NA protein.

10. The method of claim 1, wherein the molar ratio of non-ionic detergent to viral glycoprotein is about 30:1 to about 60:1.

11. The method of claim 10, wherein the RSV F protein comprises a deletion of 1 to 10 amino acids corresponding to amino acids 137-146 of SEQ ID NO:2 and an inactivated primary furin cleavage site corresponding to amino acids 131 to 136 of SEQ ID NO:2, wherein the primary furin cleavage site is inactivated by mutation.

12. The method of claim 11, wherein the composition is substantially free of any other detergent.

13. The method of claim 11, wherein the RSV-F protein is selected from the group consisting of SEQ ID NOS:2-13 and variants of SEQ ID NOS:2-13 lacking part or all of the N-terminal signal peptide.

14. The method of claim 13, wherein the RSV F protein consists of SEQ ID NO:19.

15. The method of claim 14, wherein the non-ionic detergent is PS80.

16. A method of reducing exacerbations of chronic obstructive pulmonary disease (COPD) in response to an environmental insult in a human having COPD comprising administering an immunogenic composition to the human, wherein the immunogenic composition comprises a first nanoparticle, wherein the first nanoparticle comprises a PS80 non-ionic detergent core and a first viral glycoprotein, wherein the viral glycoprotein is associated with the core and the detergent is present at about 0.03% to about 0.05%, wherein the first viral glycoprotein is an RSV F glycoprotein.

17. The method of claim 16 wherein the RSV-F protein is selected from the group consisting of SEQ ID NOS:2-13 and variants of SEQ ID NOS:2-13 lacking part or all of the N-terminal signal peptide.

18. The method of claim 17 wherein the immunogenic composition comprises a second nanoparticle wherein the second nanoparticle comprises a PS80 non-ionic detergent core and a second viral glycoprotein, wherein the second viral protein is an influenza HA protein.

* * * * *